(12) United States Patent
Hee-Hanson et al.

(10) Patent No.: US 12,357,758 B1
(45) Date of Patent: Jul. 15, 2025

(54) MEDICAMENT DELIVERY DEVICE

(71) Applicant: Genzyme Corporation, Cambridge, MA (US)

(72) Inventors: Alexander Hee-Hanson, Melbourn (GB); Michael Parrott, Melbourn (GB); Nicholas Harding, Melbourn (GB); Robert Wilson, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/640,292

(22) Filed: Apr. 19, 2024

(51) Int. Cl.
*A61M 5/20* (2006.01)
*A61M 5/32* (2006.01)

(52) U.S. Cl.
CPC ........ *A61M 5/2033* (2013.01); *A61M 5/3216* (2013.01); *A61M 2205/3368* (2013.01)

(58) Field of Classification Search
CPC .... A61M 5/315; A61M 5/31501–2005/31508; A61M 5/31571; A61M 5/50–2005/5093; B65D 55/02–145
USPC ........................................................ 220/201
See application file for complete search history.

(56) References Cited

U.S. PATENT DOCUMENTS

| | | | |
|---|---|---|---|
| 2,522,961 A * | 9/1950 | Rabak ................ | B65D 17/4011 220/359.1 |
| 2,633,267 A * | 3/1953 | Lebus ................. | B65D 25/385 220/88.1 |
| 3,886,513 A | 5/1975 | Smith et al. | |

(Continued)

FOREIGN PATENT DOCUMENTS

| | | | | |
|---|---|---|---|---|
| DE | 3921747 A1 * | 1/1991 | ...... | F01P 2011/0261 |
| EP | 3501577 A1 | 6/2019 | | |

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Bhisma Mehta
*Assistant Examiner* — Adam J. Cermak
(74) *Attorney, Agent, or Firm* — Fish & Richardson P.C.

(57) ABSTRACT

A medicament delivery device includes a first component, a second component configured to be movable with respect to the first component, and a temperature-dependent interconnect configured to resist movement of the first component relative to the second component. The temperature-dependent interconnect includes an engagement member and a temperature-dependent material configured to engage each other. The temperature-dependent material has a temperature-dependent material characteristic such that the temperature-dependent material has (i) a first material characteristic at a first temperature of the temperature-dependent material to resist movement of the first component with respect to the second component, and (ii) a second material characteristic at a second temperature of the temperature-dependent material to allow movement of the first component with respect to the second component.

27 Claims, 7 Drawing Sheets

(56) References Cited

U.S. PATENT DOCUMENTS

| | | | |
|---|---|---|---|
| 4,801,295 A * | 1/1989 | Spencer | A61M 5/50 604/199 |
| 5,045,062 A * | 9/1991 | Henson | A61M 5/5013 604/110 |
| 5,176,275 A * | 1/1993 | Bowie | D06F 39/024 68/17 R |
| 5,328,484 A * | 7/1994 | Somers | A61M 5/3202 604/196 |
| 5,396,051 A * | 3/1995 | Kuhn | B65D 81/3453 219/679 |
| 5,478,316 A * | 12/1995 | Bitdinger | A61M 5/2033 604/157 |
| 5,505,324 A * | 4/1996 | Danico | B62D 25/24 220/359.4 |
| 5,505,706 A | 4/1996 | Maus et al. | |
| 5,536,917 A * | 7/1996 | Suppelsa | B29C 66/54 156/752 |
| 5,622,274 A * | 4/1997 | Bright | B29C 45/0055 215/320 |
| 5,738,658 A * | 4/1998 | Maus | F03G 7/06 60/527 |
| 5,984,899 A | 11/1999 | D'Alessio et al. | |
| 6,080,461 A * | 6/2000 | Wozniak | A61M 5/5013 604/110 |
| 6,394,985 B1 * | 5/2002 | Lin | A61M 5/5013 604/238 |
| 7,762,981 B2 * | 7/2010 | Dacquay | A61M 5/14546 604/233 |
| 7,887,506 B1 * | 2/2011 | Smolyarov | A61M 5/30 604/68 |
| 7,918,824 B2 | 4/2011 | Bishop et al. | |
| 8,133,198 B2 * | 3/2012 | Neer | A61M 5/145 604/131 |
| 8,409,138 B2 | 4/2013 | James et al. | |
| 8,734,394 B2 | 5/2014 | Adams et al. | |
| 9,044,553 B2 | 6/2015 | James et al. | |
| 9,402,957 B2 | 8/2016 | Adams et al. | |
| 9,872,961 B2 | 1/2018 | Fourt et al. | |
| 10,118,001 B2 | 11/2018 | Fourt et al. | |
| 10,314,981 B2 * | 6/2019 | Sampson | A61M 5/20 |
| 10,350,362 B2 | 7/2019 | Dennis, Jr. et al. | |
| 10,363,377 B2 | 7/2019 | Atterbury et al. | |
| 11,298,462 B2 | 4/2022 | Atterbury et al. | |
| 11,331,432 B2 | 5/2022 | Holmqvist et al. | |
| 11,369,751 B2 * | 6/2022 | Ruan | A61M 5/3272 |
| 11,452,821 B2 | 9/2022 | LaFever et al. | |
| 2002/0055712 A1 * | 5/2002 | Neracher | A61M 5/31525 604/153 |
| 2004/0039336 A1 * | 2/2004 | Amark | A61M 5/2033 604/137 |
| 2005/0101919 A1 | 5/2005 | Brunnberg | |
| 2005/0273061 A1 | 12/2005 | Hommann et al. | |
| 2006/0224124 A1 | 10/2006 | Scherer | |
| 2007/0270777 A1 * | 11/2007 | Dacquay | A61M 5/445 604/521 |
| 2008/0097311 A1 * | 4/2008 | Dacquay | A61M 5/1452 604/113 |
| 2008/0097390 A1 * | 4/2008 | Dacquay | A61F 9/0017 604/521 |
| 2008/0269692 A1 | 10/2008 | James et al. | |
| 2009/0036868 A1 * | 2/2009 | Pinedjian | A61F 9/0017 604/220 |
| 2009/0281496 A1 | 11/2009 | Matusch | |
| 2010/0211005 A1 * | 8/2010 | Edwards | A61M 15/008 604/82 |
| 2011/0054414 A1 | 3/2011 | Shang et al. | |
| 2011/0144594 A1 | 6/2011 | Sund et al. | |
| 2011/0202011 A1 | 8/2011 | Wozencroft | |
| 2011/0319813 A1 * | 12/2011 | Kamen | A61M 5/385 604/151 |
| 2013/0237921 A1 | 9/2013 | Lannan et al. | |
| 2013/0267897 A1 | 10/2013 | Kemp et al. | |
| 2014/0236076 A1 | 8/2014 | Marshall et al. | |
| 2014/0249483 A1 * | 9/2014 | Kiilerich | A61M 5/31501 604/220 |
| 2014/0263156 A1 * | 9/2014 | Newsom | B65D 55/02 215/230 |
| 2014/0276637 A1 * | 9/2014 | Massey, Jr. | A61M 5/2448 604/82 |
| 2015/0246180 A1 | 9/2015 | Fenlon et al. | |
| 2015/0273162 A1 | 10/2015 | Holmqvist | |
| 2016/0001015 A1 * | 1/2016 | Küçük | A61M 5/5086 604/110 |
| 2016/0354555 A1 | 12/2016 | Gibson et al. | |
| 2016/0367763 A1 | 12/2016 | Tschirren et al. | |
| 2017/0215699 A1 * | 8/2017 | Ouyang | A61B 1/00045 |
| 2017/0216526 A1 | 8/2017 | Brereton et al. | |
| 2017/0224929 A1 * | 8/2017 | Sampson | A61M 5/24 |
| 2017/0246403 A1 | 8/2017 | Cowe et al. | |
| 2017/0361034 A1 * | 12/2017 | Scheller | A61B 17/3494 |
| 2018/0250471 A1 | 9/2018 | Grimoldby et al. | |
| 2018/0339114 A1 | 11/2018 | Wendland et al. | |
| 2019/0030249 A1 | 1/2019 | Gonzalez et al. | |
| 2019/0192785 A1 * | 6/2019 | Wendland | A61M 5/3213 |
| 2019/0366000 A1 | 12/2019 | Cowe et al. | |
| 2020/0114041 A1 * | 4/2020 | Alas | A61M 5/31501 |
| 2020/0316314 A1 * | 10/2020 | Buri | A61M 5/3287 |
| 2021/0077732 A1 * | 3/2021 | Egelhofer | A61M 5/5086 |
| 2021/0196900 A1 * | 7/2021 | Appy | A61M 5/3234 |
| 2022/0015429 A1 | 1/2022 | Brown et al. | |
| 2022/0176042 A1 | 6/2022 | Belisle | |
| 2022/0395640 A1 * | 12/2022 | Schwartzentruber | A61M 5/20 |
| 2023/0001099 A1 * | 1/2023 | Dunn | A61M 5/3202 |
| 2023/0238105 A1 | 7/2023 | Schneider et al. | |
| 2023/0347074 A1 * | 11/2023 | Gavin | A61M 5/3135 |
| 2024/0009397 A1 * | 1/2024 | In | A61M 5/2425 |

FOREIGN PATENT DOCUMENTS

| | | |
|---|---|---|
| WO | WO 2002/047746 A1 | 6/2002 |
| WO | WO 2011/109205 A2 | 9/2011 |
| WO | WO 2016/081238 A1 | 5/2016 |
| WO | WO 2019/074788 A1 | 4/2019 |
| WO | WO 2020/190529 A1 | 9/2020 |

OTHER PUBLICATIONS

U.S. Appl. No. 18/640,163, filed Apr. 19, 2024, Alexander Hee-Hanson.

U.S. Appl. No. 18/640,427, filed Apr. 19, 2024, Alexander Hee-Hanson.

U.S. Appl. No. 18/640,600, filed Apr. 19, 2024, Alexander Hee-Hanson.

U.S. Appl. No. 18/640,710, filed Apr. 19, 2024, Alexander Hee-Hanson.

* cited by examiner

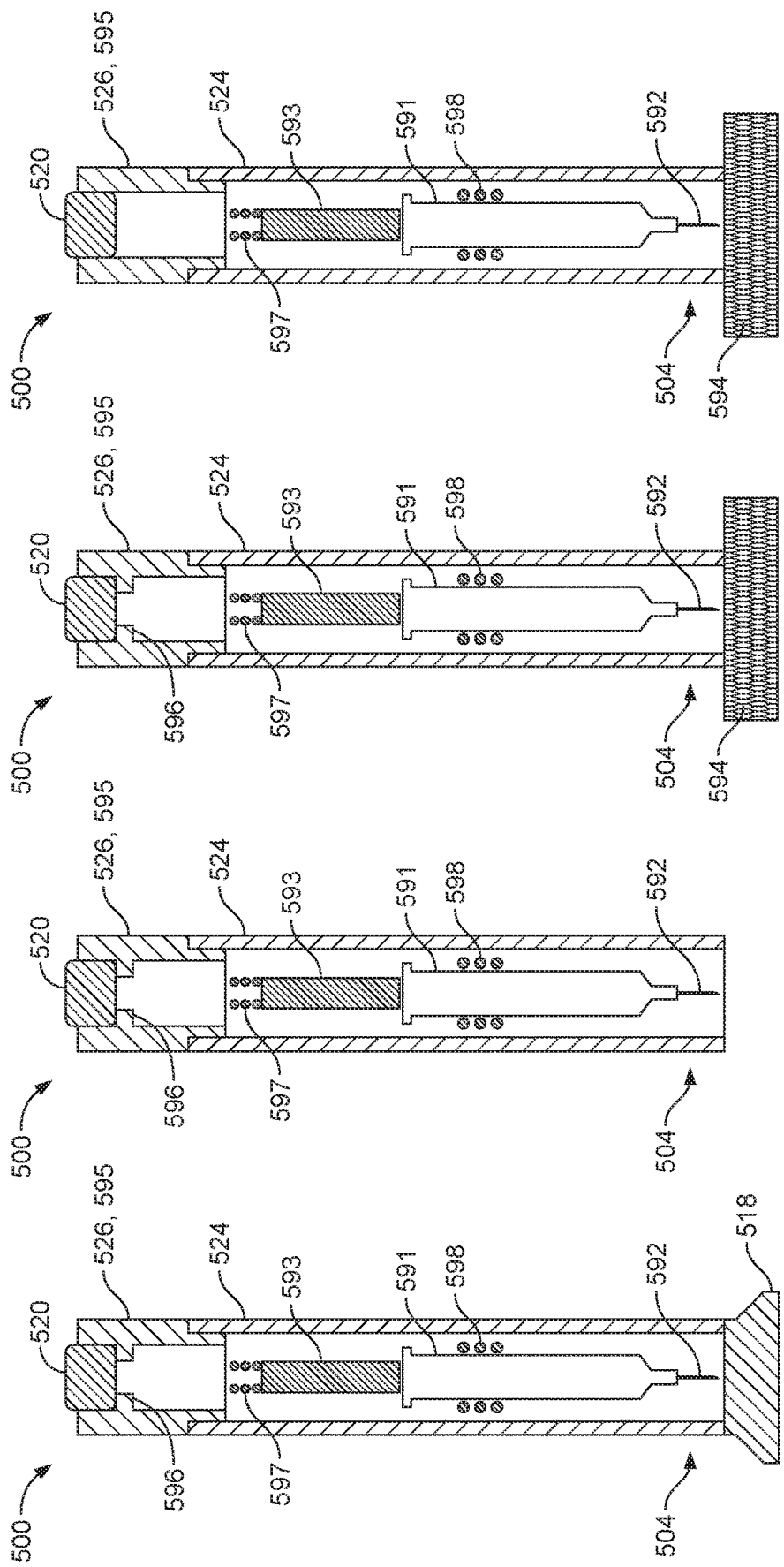

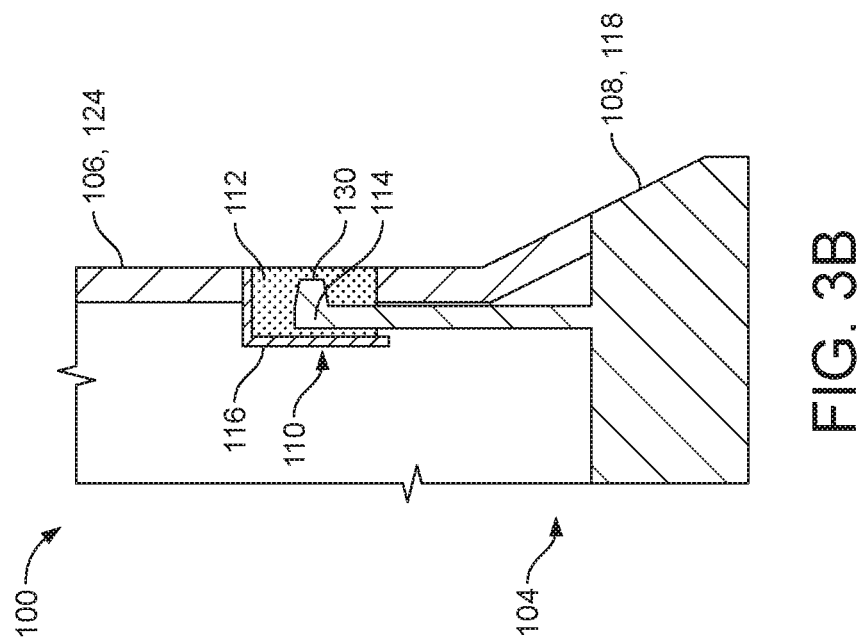
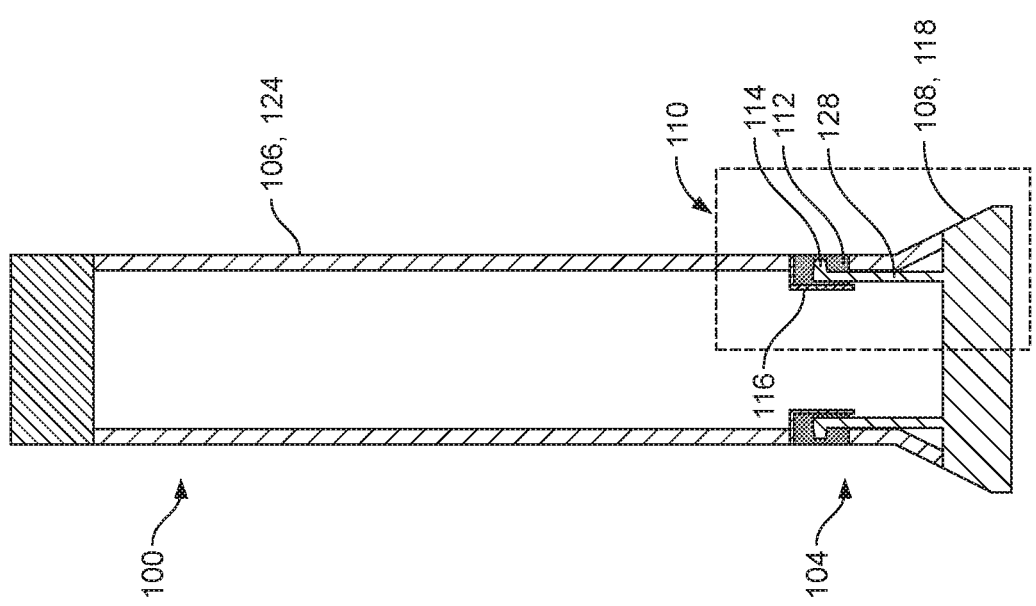

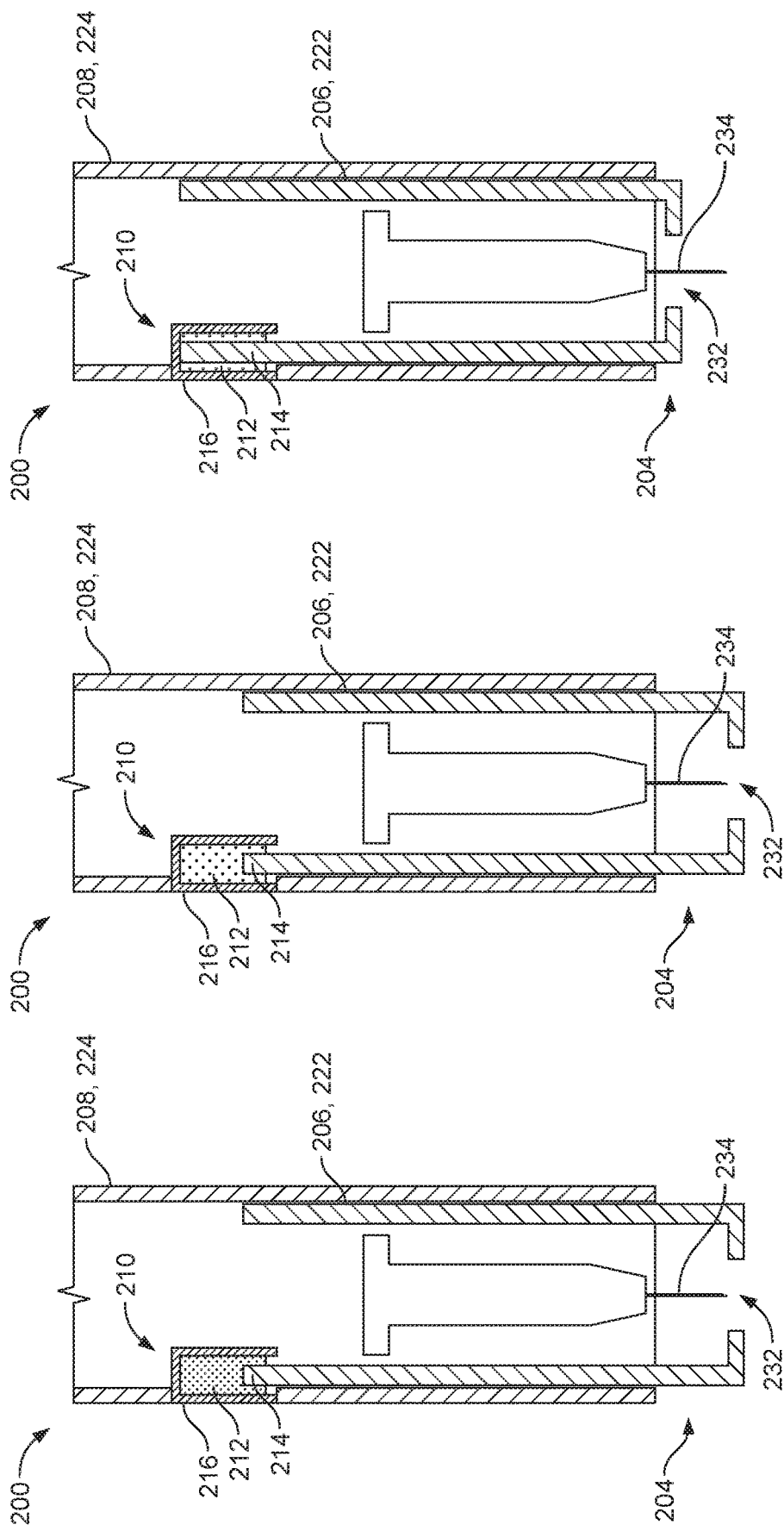

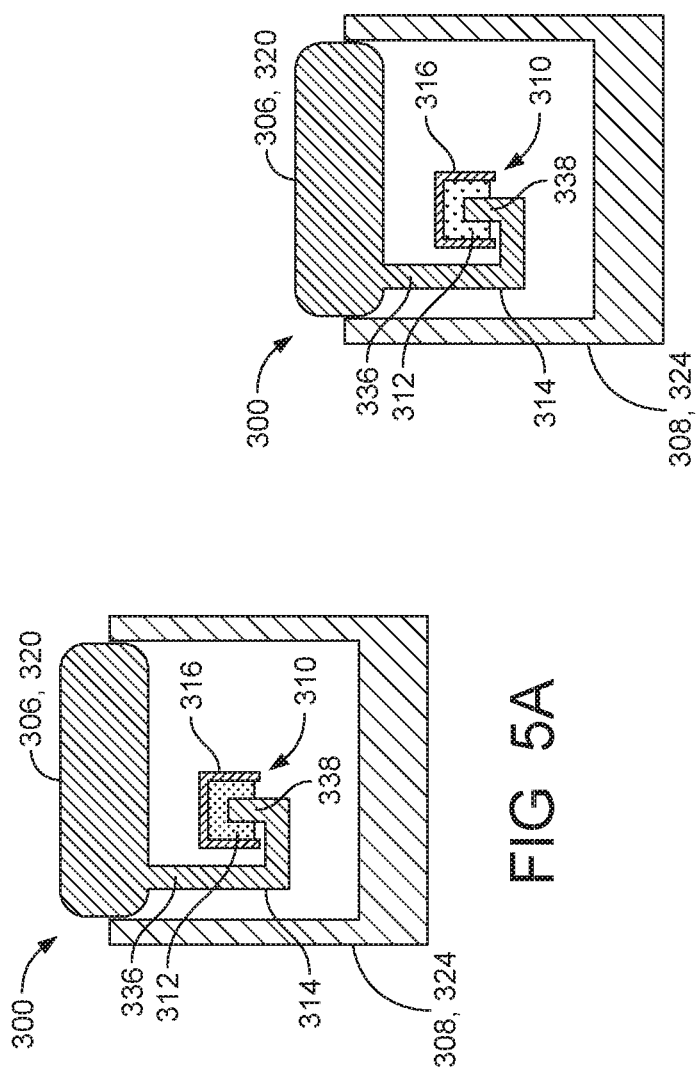
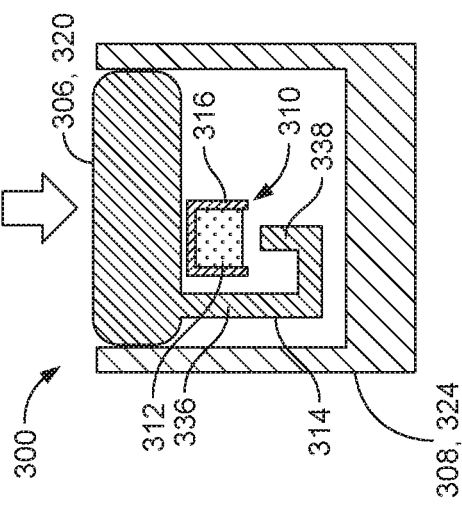
FIG. 5A
FIG. 5B
FIG. 5C

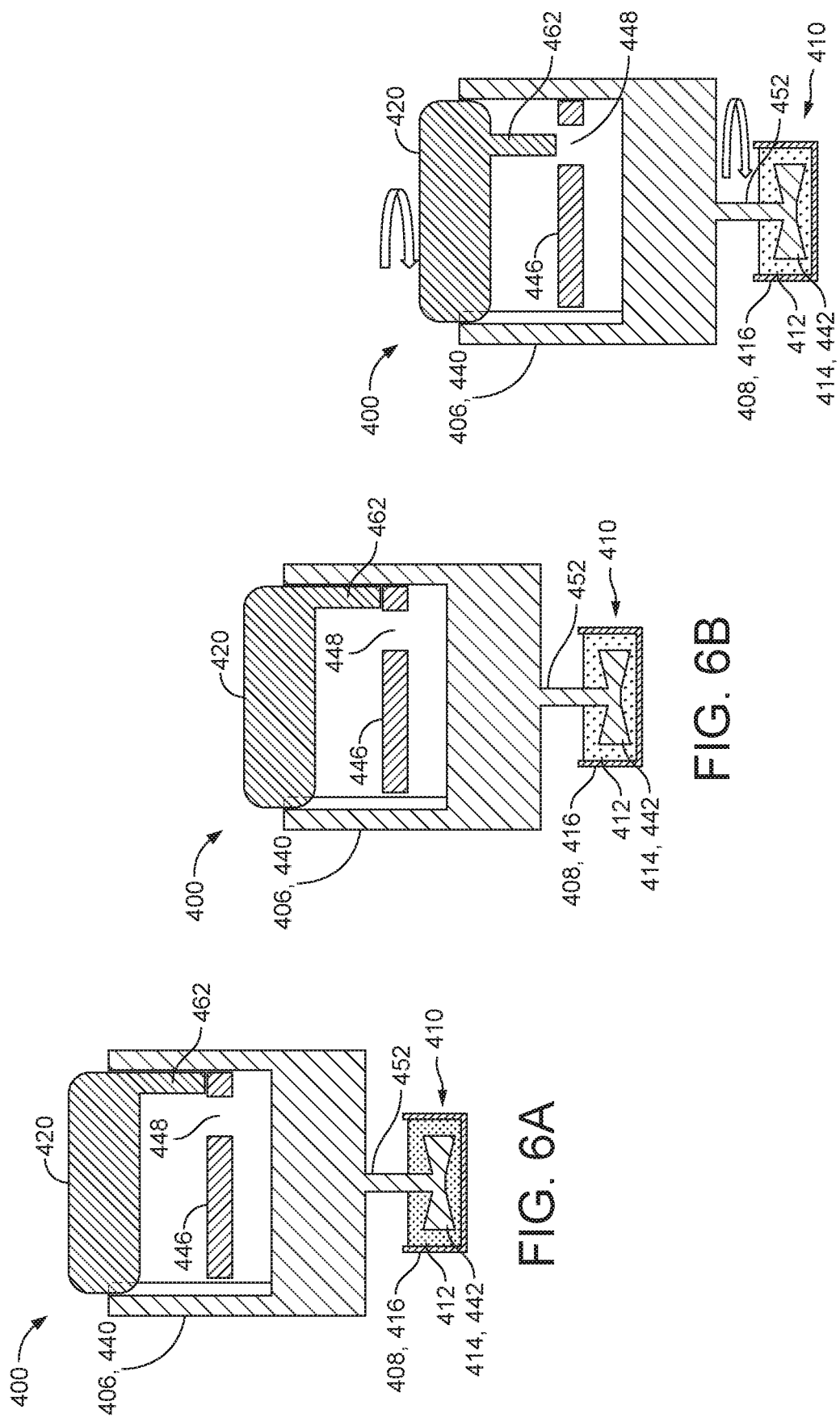

MEDICAMENT DELIVERY DEVICE

TECHNICAL FIELD

The present disclosure relates to a medicament delivery device and to a method of using a medicament delivery device.

BACKGROUND

Medicament delivery devices, such as auto-injectors, dispense medicament to an injection site of a patient.

Some devices may be triggered when the device is at a sub-optimal temperature. Dependent on the particular medicament within the device, some medicament delivery devices are required to be stored at sub-ambient temperatures, for example in a fridge or in a freezer, in order to allow the medicament to be stored for an extended period of time without the medicament losing efficacy. When the medicament is too cold, for example if it has not been allowed to warm to ambient temperature, the viscosity of the medicament may be increased such that a dose may be dispensed incorrectly or not at all, for example the viscosity of the medicament may be such that the medicament is unable to pass through a needle of the device. Thus, when a user places the device at an injection site and triggers the device, expecting a dose of medicament to be delivered, a dose may not be dispensed or may not be fully dispensed. In some instances, the user may not be aware that a dose was not dispensed or that a dose was improperly or not fully dispensed. The user may then remove the device from the injection site and the device may then increase in temperature through being passively heated by the external environment, for example to ambient temperature, causing the viscosity of the medicament to decrease and causing the already-triggered device to unexpectedly dispense a dose of medicament. Furthermore, the dispensing of medicament when the medicament is too cold can be painful to a recipient or subject of the injection.

SUMMARY

According to a first aspect, a medicament delivery device includes:
a first component;
a second component configured to be movable with respect to the first component;
a temperature-dependent interconnect configured to resist movement of the first component relative to the second component;
the temperature-dependent interconnect comprising:
an engagement member and a temperature-dependent material, wherein the engagement member is configured to engage the temperature-dependent material;
the temperature-dependent material having a temperature-dependent material characteristic such that the temperature-dependent material has:
a first material characteristic at a first temperature of the temperature-dependent material so as to resist movement of the first component with respect to the second component, and;
a second material characteristic at a second temperature of the temperature-dependent material so as to facilitate movement of the first component with respect to the second component such that a force required to move the first component with respect to the second component at the second temperature is (e.g. substantially) less than at the first temperature;
wherein the second temperature is greater (i.e. more positive, or higher) than the first temperature.

In some embodiments, the first characteristic of the temperature-dependent material is such that movement of the engagement member with respect to the temperature-dependent material is resisted by the temperature-dependent material.

In some embodiments, the first characteristic of the temperature-dependent material is such that movement of the engagement member with respect to the temperature-dependent material is substantially prevented by the temperature-dependent material.

In some embodiments, the second characteristic of the temperature-dependent material is such that movement of the engagement member, e.g. with respect to the temperature-dependent material is facilitated.

In some embodiments, the temperature-dependent material is provided within a reservoir, and wherein the first characteristic of the temperature-dependent material is such that movement of the engagement member with respect to a reservoir of the device is resisted by the temperature-dependent material.

In some embodiments, the temperature-dependent material is provided within a reservoir, and wherein the second characteristic of the temperature-dependent material is such that movement of the engagement member with respect to a reservoir of the device is facilitated.

In some embodiments, the first characteristic of the temperature-dependent material is such that movement of the engagement member with respect to the temperature-dependent material is substantially prevented and/or the first characteristic of the temperature-dependent material is such that movement of the first component with respect to the second component is substantially prevented.

In some embodiments, the second characteristic of the temperature-dependent material allows movement of the engagement member with respect to the temperature-dependent material and/or the second characteristic of the temperature-dependent material allows movement of the first component with respect to the second component.

In some embodiments, movement of the first component with respect to the second component causes the engagement member to move with respect to the temperature-dependent material. In some embodiments, movement of the first component with respect to the second component causes the engagement member to move with respect to a reservoir of the device, the temperature-dependent material being provided within the reservoir at the first temperature.

In some embodiments, a force required to move the engagement member with respect to the temperature-dependent material at the second temperature is less than at the first temperature. In some embodiments, a force required to move the engagement member with respect to a reservoir, the temperature-dependent material being provided in the reservoir at the first temperature, at the second temperature is less than at the first temperature.

In some embodiments, the temperature-dependent interconnect is configured to connect the first component to the second component.

In some embodiments, the engagement member is configured to (e.g. interlockingly) interconnect with (e.g. be received by or within) the temperature-dependent material so as to resist movement of the first component with respect to the second component.

In some embodiments, the medicament delivery device further comprises a reservoir and the temperature-dependent material is provided within the reservoir, e.g. at the first temperature. In some embodiments, the temperature-dependent material is contained within the reservoir, e.g. at the first temperature. In some embodiments, the temperature-dependent material is caused to escape the reservoir at the second temperature.

In some embodiments, the engagement member is configured to be movable through the reservoir at the second temperature. In some embodiments, movement of the engagement member through the reservoir at the first temperature is resisted compared to at the second temperature.

In some embodiments, the first component comprises the temperature-dependent material and the second component comprises the engagement member. In some embodiments, the temperature-dependent material and/or engagement member are operatively coupled to, e.g. attached to (either directly or indirectly), a respective one of the first or second components.

In some embodiments, the material characteristic is a viscosity of the temperature-dependent material and the viscosity of the temperature-dependent material at the first temperature is greater than at the second temperature.

In some embodiments, the material characteristic is a phase of the temperature-dependent material and, at the first temperature, the temperature-dependent material is in a solid or liquid phase and, at the second temperature, the temperature-dependent material is in a liquid or gaseous phase. In some embodiments, at the first temperature the temperature-dependent material is in a solid phase and at the second temperature the temperature-dependent material is in a liquid phase. In some embodiments, at the first temperature the temperature-dependent material is in a solid phase and at the second temperature the temperature-dependent material is in a gaseous phase. In some embodiments, at the first temperature the temperature-dependent material is in a liquid phase and at the second temperature the temperature-dependent material is in a gaseous phase.

In some embodiments, the temperature-dependent material is in the same phase at both the first and second temperatures, for example the temperature-dependent material is in a solid phase, a liquid phase or a gaseous phase at both the first and second temperatures. In some embodiments, the material characteristic is a density of the temperature-dependent material and the density of the temperature-dependent material at the first temperature is greater than at the second temperature.

In some embodiments, the material characteristic is a material stiffness of the temperature-dependent material and the material stiffness of the temperature-dependent material at the first temperature is greater than at the second temperature.

In some embodiments, the material characteristic is an adhesiveness of the temperature-dependent material and the adhesiveness of the temperature-dependent material at the first temperature is greater than at the second temperature.

In some embodiments, the first component comprises a detachably attachable cap (for example for covering a distal end of the device and/or for covering a needle of the device) and the temperature-dependent interconnect is configured to resist removal of the cap from the device (e.g. from a body or housing of the device, e.g. from a distal end of the housing) at the first temperature but to facilitate removal of the cap at the second temperature such that a force required to remove the cap is less at the second temperature than at the first temperature.

In some embodiments, the second component comprises a body (e.g. a housing) and one of the body and the cap comprises the temperature-dependent material and the other one of the body and the cap comprises the engagement member.

In some embodiments, the first component comprises an actuation member (such as a button), the actuation member is configured to be movable (e.g. depressible) by a user from a first position to an actuation position for dispensing medicament from the device, and the temperature-dependent interconnect is configured to resist movement of the actuation member from the first position to the actuation position at the first temperature but to facilitate movement of the actuation member from the first position to the actuation position at the second temperature such that a force required to move the actuation member from the first position to the actuation position is less at the second temperature than at the first temperature.

In some embodiments, the second component comprises a body (e.g. a housing) and one of the body and the actuation member comprises the temperature-dependent material and the other comprises the engagement member. In some embodiments, the actuation member comprises the engagement member and, when the actuation member moves from the first position to the actuation position, the engagement member is caused to move with respect to the temperature-dependent material. In some embodiments, the engagement member comprises a leg configured to extend from the actuation member into the reservoir so as to engage the temperature-dependent material when the actuation member is in the first position.

In some embodiments, the first component comprises a needle sleeve configured to be axially moveable in a proximal direction from an extended position in which the needle sleeve extends from a distal end of the device to a retracted position, and the temperature-dependent interconnect is configured to resist axial movement of the needle sleeve from the extended position to the retracted position at the first temperature but to facilitate movement of the needle sleeve from the extended position to the retracted position at the second temperature such that a force required to move the needle sleeve from the extended position to the retracted position is less at the second temperature than at the first temperature.

In some embodiments, the second component comprises a body (e.g. a housing), and one of the needle sleeve (e.g. a proximal end thereof) and the body comprises the temperature-dependent material and the other one of the needle sleeve and the body comprises the engagement member. In some embodiments, the proximal end of the needle sleeve comprises the engagement member. In some embodiments, the engagement member is configured to engage the temperature-dependent material when the needle sleeve is in the extended and/or retracted position.

In some embodiments, the needle sleeve is configured such that movement of the needle sleeve from the extended position to the retracted position causes the dispensing of medicament from the device. In some embodiments, the needle sleeve is configured such that axial movement of the needle sleeve from the extended position to the retracted position triggers a mechanism configured to dispense medicament from the device.

In some embodiments, the medicament delivery device further comprises:
  an actuation member configured to be moveable by a user to an actuation position to cause medicament to be dispensed from the medicament delivery device;

wherein the first component comprises a locking member configured to prevent movement of the actuation member to the actuation position, the locking member being configured to move from a locking position, in which the actuation member is prevented from moving to the actuation position, to an actuation member release position in which the actuation member is released for movement to the actuation position; and wherein the temperature-dependent interconnect is configured to resist movement of the locking member from the locking position to the actuation member release position at the first temperature but to facilitate movement of the locking member from the locking position to the actuation member release position at the second temperature such that a force required to move the locking member from the locking position to the actuator release position is less at the second temperature than at the first temperature.

In some embodiments, the second component comprises the body.

In some embodiments, one of the body and the locking member comprises the temperature-dependent material and the other one of the body and the locking member comprises the engagement member.

In some embodiments, the locking member is configured to be rotatable about a longitudinal axis of the medicament delivery device from the locking position to the actuation member release position.

In some embodiments, the engagement member is configured to rotate through the temperature-dependent material such that movement of the locking member from the locking position to the actuator release position is resisted by the temperature-dependent material at the first temperature but movement of the locking member from the locking position to the actuator release position is facilitated at the second temperature such that a force required to move the locking member from the locking position to the actuation release position is less at the second temperature than at the first temperature.

In some embodiments, the second temperature is 5 degrees Celsius or more, for example 6, 7, 8, 9, 10, 11, 12, 13, 14, 15, 16, 17, 18, 19, 20, 21, 23, 24 or 25 degrees Celsius or more, or the second temperature is within a range defined by any two of these values.

In some embodiments, the second temperature is between 8 and 25 degrees Celsius, e.g. between 10 and 15 degrees Celsius.

In some embodiments, the first temperature is 10 degrees Celsius or less, for example 10, 9, 8, 7, 6, 5, 4, 3, 2, 1, 0, −1, −2, −3, −4, −5, −6, −7, −8, −9, −10, −11, −12, −13, −14 or −15 degrees Celsius or more, or the first temperature is within a range defined by any two of these values.

In some embodiments, the first temperature is between −10 and 10 degrees Celsius, e.g. between −8 and 8 degrees Celsius.

In some embodiments, the temperature-dependent material comprises a wax, polyethylene glycol, or a salt hydrate.

In some embodiments, the material characteristic of the temperature-dependent material is temperature-reversible so as to be transitionable from the second material characteristic to the first material characteristic upon a reduction in the temperature of the temperature-dependent material, for example from the second temperature to the first temperature.

According to a second aspect, a method of using a medicament delivery device is disclosed, the medicament delivery device includes:

a first component;
a second component configured to be movable with respect to the first component;
a temperature-dependent interconnect configured to resist movement of the first component relative to the second component;
the temperature-dependent interconnect comprising:
an engagement member and a temperature-dependent material, wherein the engagement member is configured to engage the temperature-dependent material;
the temperature-dependent material having a temperature-dependent material characteristic such that the temperature-dependent material has:
a first material characteristic at a first temperature of the temperature-dependent material so as to resist movement of the first component with respect to the second component, and;
a second material characteristic at a second temperature of the temperature-dependent material so as to facilitate movement of the first component with respect to the second component such that a force required to move the first component with respect to the second component at the second temperature is (e.g. substantially) less than at the first temperature;
wherein the second temperature is greater than the first temperature;
the method comprising:
increasing the temperature of the temperature-dependent material from the first temperature to the second temperature; and
moving the first component relative to the second component.

According to a third aspect, a medicament delivery device includes a first component, a second component configured to be movable with respect to the first component, and a temperature-dependent interconnect configured to resist movement of the first component relative to the second component.

In some embodiments, the temperature-dependent interconnect includes (i) a temperature-dependent material having a temperature-dependent material characteristic such that the temperature-dependent material has (i) a first material characteristic at a first temperature of the temperature-dependent material to resist movement of the first component with respect to the second component, and (ii) a second material characteristic at a second temperature of the temperature-dependent material to allow movement of the first component with respect to the second component; and (ii) an engagement member configured to engage the temperature-dependent material.

In some embodiments, the temperature-dependent material is configured such that a force required to move the first component with respect to the second component at the second temperature is less than a force required to move the first component with respect to the second component at the first temperature, the second temperature being greater than the first temperature.

In some embodiments, the medicament delivery device further includes a reservoir in which the temperature-dependent material is disposed.

In some embodiments, the temperature-dependent material characteristic comprises a viscosity change of the temperature-dependent material. In some cases, a viscosity of the temperature-dependent material at the first temperature is greater than a viscosity of the temperature-dependent material at the second temperature.

In some embodiments, the temperature-dependent material characteristic comprises a phase change of the temperature-dependent material. In some cases, when the temperature-dependent material is at the first temperature, the temperature-dependent material is in a solid phase and when the temperature-dependent material is at the second temperature, the temperature-dependent material is in a liquid phase.

In some embodiments, when the temperature-dependent material is at the first temperature, the temperature-dependent material is in a liquid phase and when the temperature-dependent material is at the second temperature, the temperature-dependent material is in a gaseous phase.

In some embodiments, the temperature-dependent material characteristic comprises a density change of the temperature-dependent material. In some cases, a density of the temperature-dependent material at the first temperature is greater than a density of the temperature-dependent material at the second temperature.

In some embodiments, the temperature-dependent material characteristic comprises a material stiffness change of the temperature-dependent material. In some cases, a material stiffness of the temperature-dependent material at the first temperature is greater than a material stiffness of the temperature-dependent material at the second temperature.

In some embodiments, the temperature-dependent material characteristic comprises an adhesiveness change of the temperature-dependent material. In some cases, an adhesiveness of the temperature-dependent material at the first temperature is greater than an adhesiveness of the temperature-dependent material at the second temperature.

In some embodiments, the first component comprises a removable cap, and the temperature-dependent interconnect is configured to (i) resist removal of the removable cap from the medicament delivery device at the first temperature and (ii) allow removal of the removable cap from the medicament delivery device at the second temperature such that a force required to remove the removable cap from the medicament delivery device at the second temperature is less than a force required to remove the removable cap from the medicament delivery device at the first temperature.

In some embodiments, the first component comprises an actuation member configured to be movable from a first position to a second position for dispensing medicament from the medicament delivery device.

In some embodiments, the temperature-dependent interconnect is configured to (i) resist movement of the actuation member from the first position to the second position at the first temperature and (ii) allow movement of the actuation member from the first position to the second position at the second temperature such that a force required to move the actuation member from the first position to the second position at the second temperature is less than a force required to move the actuation member from the first position to the second position at the first temperature.

In some embodiments, the first component comprises a needle sleeve configured to be axially moveable in a proximal direction from an extended position in which the needle sleeve extends from a distal end of the medicament delivery device to a retracted position, and the temperature-dependent interconnect is configured to (i) resist axial movement of the needle sleeve from the extended position to the retracted position at the first temperature and (ii) allow movement of the needle sleeve from the extended position to the retracted position at the second temperature such that a force required to move the needle sleeve from the extended position to the retracted position at the second temperature is less than a force required to move the needle sleeve from the extended position to the retracted position at the first temperature.

In some embodiments, the medicament delivery device further comprises an actuation member configured to be movable to an actuation position to cause medicament to be dispensed from the medicament delivery device, and the first component comprises a locking member configured to prevent movement of the actuation member to the actuation position, the locking member being configured to move from (i) a first position in which the actuation member is prevented from moving to the actuation position to (ii) a second position in which the actuation member is released for movement to the actuation position.

In some embodiments, the temperature-dependent interconnect is configured to (i) resist movement of the locking member from the first position to the second position at the first temperature and (ii) allow movement of the locking member from the first position to the second position at the second temperature such that a force required to move the locking member from the first position to the second position at the second temperature is less than a force required to move the locking member from the first position to the second position at the first temperature.

In some embodiments, the second temperature is 5 degrees Celsius or greater.

In some embodiments, the temperature-dependent material comprises a wax, polyethylene glycol, or a salt hydrate.

In some embodiments, the temperature-dependent material characteristic of the temperature-dependent material is temperature-reversible so as to be transitionable from the second material characteristic to the first material characteristic upon a reduction in a temperature of the temperature-dependent material.

According to a fourth aspect, a medicament delivery device includes a first component, a second component configured to be movable with respect to the first component, and a third component configured to limit movement of the first component relative to the second component.

In some embodiments, the third component includes a temperature-dependent material having a first material characteristic at a first temperature and a second material characteristic at a second temperature. In some cases, changing the third component from the first temperature to the second temperature causes the third component to change from limiting movement of the first component relative to the second component to allowing movement of the first component relative to the second component.

In some embodiments, the temperature-dependent material is configured such that a force required to move the first component relative to the second component at the second temperature is less than a force required to move the first component relative to the second component at the first temperature, the second temperature being greater than the first temperature.

In some embodiments, the second material characteristic represents a viscosity change relative to the first material characteristic, a phase change relative to the first material characteristic, a material stiffness change relative to the first material characteristic, an adhesiveness change relative to the first material characteristic, or a density change relative to the first material characteristic.

In some embodiments, one of the first component or the second component comprises a protrusion or arm configured to engage the temperature-dependent material of the third component for limiting movement of the first component relative to the second component when the temperature-dependent material is at the first temperature and allowing movement of the first component relative to the second component when the temperature-dependent material is at the second temperature.

According to a fifth aspect, a medicament delivery device includes a first component, a second component, and a third component. The third component configured to (i) limit movement of the first component relative to the second component when a temperature of a temperature-dependent material of the third component is at a first temperature and (ii) allow movement of the first component relative to the second component when the temperature of the temperature-dependent material of the third component is at a second temperature.

In some embodiments, the medicament delivery device is configured such that a force required to move the first component relative to the second component at the second temperature is less than a force required to move the first component relative to the second component at the first temperature, the second temperature being greater than the first temperature.

In some embodiments, the third component is attached to one of the first component or the second component and the medicament delivery device is configured such that the other of the first component or the second component is configured to move relative to the third component.

In some embodiments, one of the first component or the second component comprises a protrusion or arm configured to engage the temperature-dependent material of the third component for limiting movement of the first component relative to the second component when the temperature of the temperature-dependent material is at the first temperature and allowing movement of the first component relative to the second component when the temperature of the temperature-dependent material is at the second temperature.

According to a sixth aspect, a method includes the following steps (i) while a temperature-dependent material of a medicament delivery device is at a first temperature, resisting movement of a first component of the medicament delivery device relative to a second component; (ii) increasing a temperature of the temperature-dependent material from the first temperature to a second temperature to allow movement of the first component relative to the second component; and (iii) while the temperature-dependent material is at the second temperature, moving the first component relative to the second component.

In some embodiments, the method includes decreasing the temperature of the temperature-dependent material from the second temperature to the first temperature to limit movement of the first component relative to the second component.

BRIEF DESCRIPTION OF THE DRAWINGS

Embodiments will now be described, by way of example, with reference to the accompanying drawings, in which:

FIG. 2A is a schematic view of a medicament delivery device prior to use (i.e. in a pre-use configuration);

FIG. 2B is a schematic view of the device of FIG. 2A with a cap thereof removed;

FIG. 2C is a schematic view of the device of FIG. 2A showing the device placed at an injection site;

FIG. 2D is a schematic view of the device of FIG. 2A with a locking member of the device having been rotated so as to allow a button of the device to be depressed by a user;

FIG. 3A is a schematic cross-sectional view of parts of a device according to a first embodiment having a detachably attachable cap attached to a body of the device by a temperature-dependent interconnect;

FIG. 3B is a close-up cross-sectional schematic view of the temperature-dependent interconnect of the device of FIG. 3A;

FIG. 4A is a schematic cross-sectional view of parts of a device according to a second embodiment having an axially moveable needle sleeve connected to a body of the device by a temperature-dependent interconnect, the temperature-dependent interconnect being at a first temperature and the needle sleeve being in an extended position;

FIG. 4B is a schematic cross-sectional view of parts of the device of FIG. 4A, the temperature-dependent interconnect being at a second temperature, greater than the first temperature, and the needle sleeve being in an extended position;

FIG. 4C is a schematic cross-sectional view of parts of the device of FIG. 4A, the temperature-dependent interconnect being at the second temperature, and the needle sleeve being in a retracted or depressed position;

FIG. 5A is a schematic cross-sectional view of parts of a device according to a third embodiment having an actuation member connected to a body of the device by a temperature-dependent interconnect, the temperature-dependent interconnect being at a first temperature and the actuation member being in a first, raised position;

FIG. 5B is a schematic cross-sectional view of parts of the device of FIG. 5A, the temperature-dependent interconnect being at a second temperature, greater than the first temperature, and the actuation member being in a first, raised position;

FIG. 5C is a schematic cross-sectional view of parts of the device of FIG. 5A, the temperature-dependent interconnect being at the second temperature, and the actuation member having been depressed to an actuation position;

FIG. 6A is a schematic cross-sectional view of parts of a device according to a fourth embodiment having an actuation member movable from a first position to an actuation position and a rotatable locking member, the rotatable locking member being connected to a body of the device by a temperature-dependent interconnect, the temperature-dependent interconnect being at a first temperature and locking member being in a locking position so as to prevent the actuation member from being moved to the actuation position;

FIG. 6B is a schematic cross-sectional view of parts of the device of FIG. 6A, the temperature-dependent interconnect being at a second temperature, greater than the first temperature, and the locking member being in the locking position; and FIG. 6C is a schematic cross-sectional view of parts of the device of FIG. 6A, the temperature-dependent interconnect being at the second temperature, and the locking member being in an actuation member release position so as to allow the actuation member to be moved to the actuation position.

DETAILED DESCRIPTION

Figure 1A:
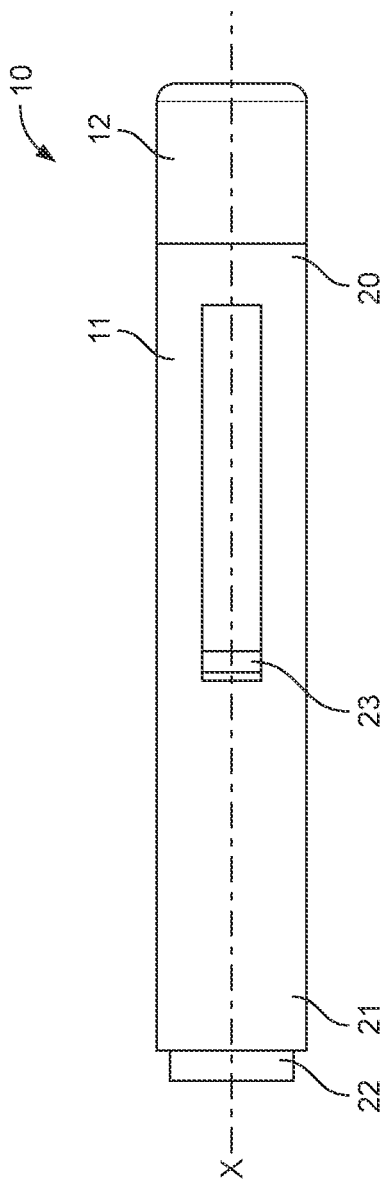
FIG. 1A is a schematic view of a medicament delivery device with a cap attached.

A drug delivery device, as described herein, may be configured to inject a medicament into a patient. For example, delivery could be sub-cutaneous, intra-muscular, or intravenous. Such a device could be operated by a patient or a care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
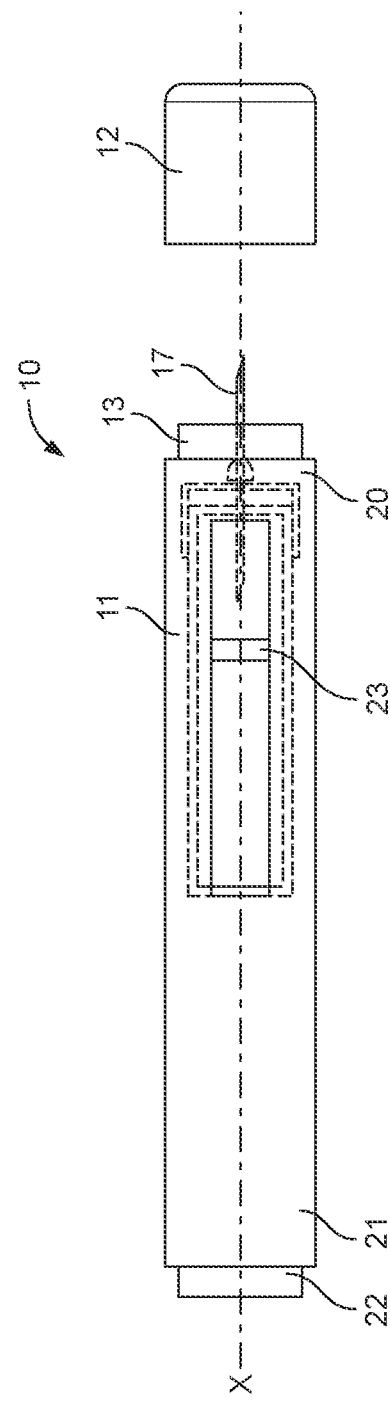
FIG. 1B is a schematic view of the medicament delivery device of FIG. 1A with the cap removed.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11. Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIGS. 2A to 2G show the sequential steps of operating a medicament injection device 500.

As shown in FIG. 2A, the device 500 comprises a body 524, a syringe 591 having a needle 592 and an axially moveable plunger 593 for dispensing medicament from the syringe 591. The device comprises a cap 518 which is removably attached to the device 500 and which covers a distal end 504 of the body 524 so as to prevent stick injuries.

As shown in FIGS. 2B-2C, in order to deliver a dose of medicament to an injection site 594, the cap 518 is removed (FIG. 2B) and the device is placed at the injection site 594 (FIG. 2C). An actuation member 520 in the form of a button 520 is prevented from being depressed by a locking member 526 in the form of a lock ring 595 which is rotatable by a user about a longitudinal axis of the device, by a radially-projecting stop 596. The stop 596 may be provided in the locking member 526 or the stop 596 may be provided on a separate part of the device. As shown in FIG. 2D, in order to allow the button 520 to be depressed by a user, the lock ring 595 is rotated about the longitudinal axis of the device to an actuation member release position (or button release position) in which the stop 596 no longer prevents the button 520 from being depressed by a user.

Figure 2G:
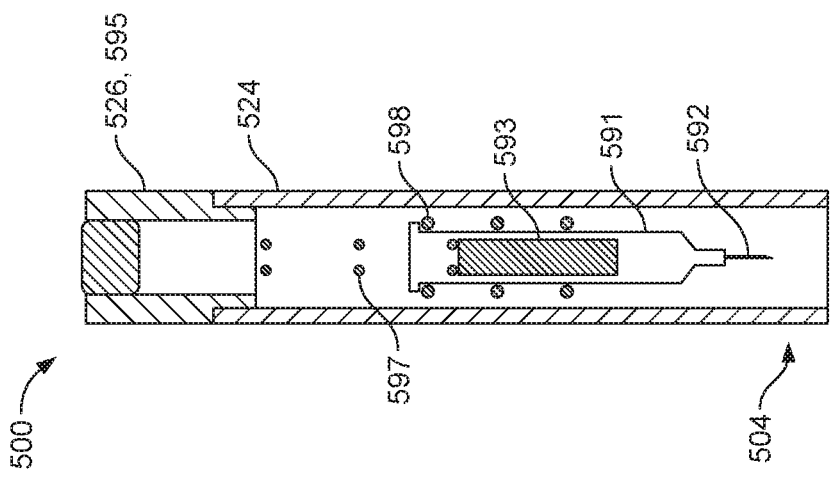
FIG. 2G is a schematic view of the device of FIG. 2A showing the device having been removed from the injection site after the needle has retracted within the device after delivery of the dose.
Figure 2F:
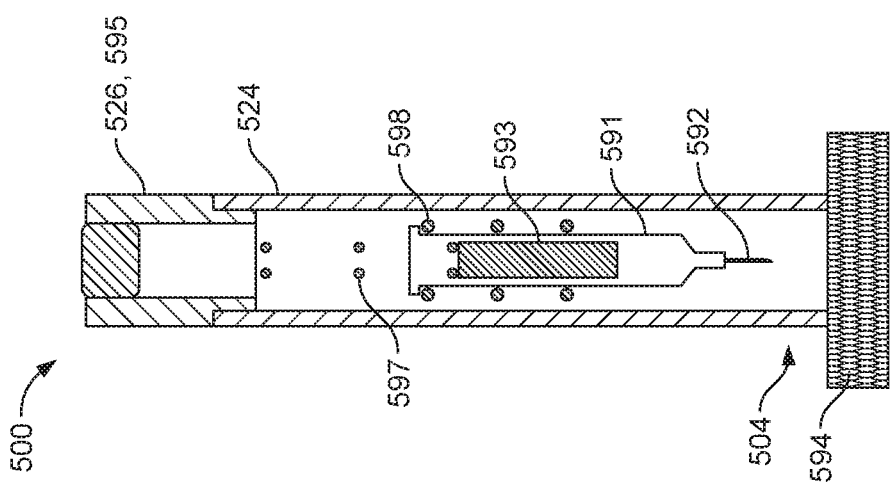
FIG. 2F is a schematic view of the device of FIG. 2A showing the needle having retracted within the device after a dose has been delivered.
Figure 2E:
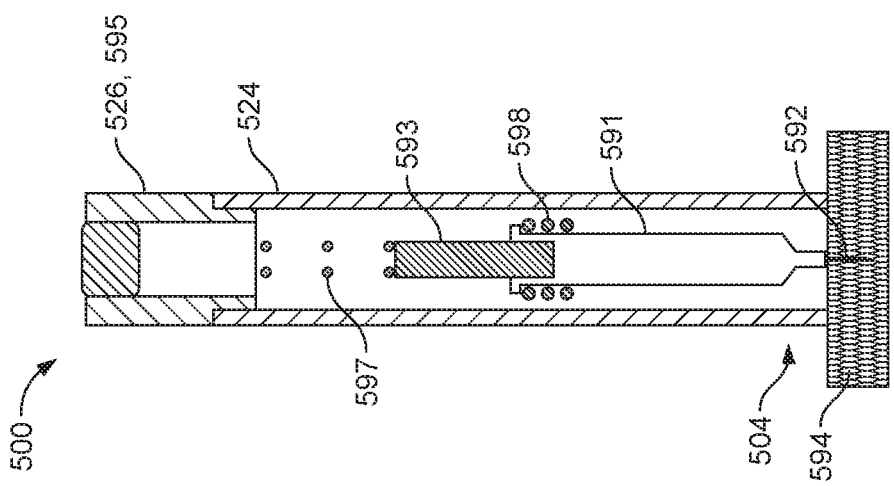
FIG. 2E is a schematic view of the device of FIG. 2A after the button has been depressed and the needle has been caused to move to an exposed position.

Turning now to FIG. 2E, the user then depresses the button 520 to an actuation position to actuate or trigger a needle mechanism so as to release the syringe 591 for distal axial movement towards the injection site 594 such that the needle 592 moves from a pre-use retracted position to an exposed (or "uncovered") position for delivering medicament to the injection site 594. The syringe 591 is moved distally so as to move the needle 592 thereof to the exposed position under a biasing force provided by a bias 597 in the form of a compression spring 597. Depressing the button 520 also releases the plunger 593 which, biased by the bias 597, moves along the syringe 591 towards the distal end 504 of the device 500 to force medicament within the syringe 591 through the needle 592, thereby delivering a dose of medicament. Thus, the bias 597 causes both the syringe 592 to move distally so as to move the needle 592 thereof to the exposed position and also causes the plunger 593 to move within the syringe 591 so at to cause a dose of medicament within the syringe 591 to be dispensed through the needle 592. As shown in FIG. 2F, once the dose has been delivered, a medicament container bias 598, embodied by a further spring 598, then causes the needle 592 to move axially back to the retracted position, away from the injection site 594 in a proximal direction. As shown in FIG. 2G, the device 500 is then removed from the injection site 594 for later reuse or for disposal.

Turning now to FIGS. 3A and 3B, parts of a first embodiment of medicament delivery device 100 are shown. For ease of illustration, parts of the medicament delivery device 100 are shown, but it will be appreciated that the device 100 of the first embodiment may be provided with one or more of the other parts of the device 500 discussed with reference to FIGS. 2A-2G and in certain embodiments, the device 100 of the first embodiment can be considered to be a modification of the device 500.

The medicament delivery device 100 of the first embodiment comprises a first component 106 which in this embodiment is embodied as a body (or housing) 124 and a second component 108 which in this embodiment is embodied as a cap 118 configured to be detachably attachable to a distal end 104 of the body 124. In certain embodiments, the cap 118 may be configured to cover a needle of the device 100 so as to prevent stick injuries. The cap 118 is manually removed by a user prior to the device being applied to an injection site for delivering a dose of medicament. Thus, the cap 118 is configured to be movable (i.e. removable) with respect to the body 124.

The device 100 further comprises a temperature-dependent interconnect 110 configured to connect or fix the cap 118 to the body 124 so as to resist removal of the cap 118 from the body 124. The temperature-dependent interconnect 110 comprises a temperature-dependent material 112, which in this embodiment is provided in a reservoir 116, and an engagement member 114 configured to engage the temperature-dependent material when the cap 118 is attached to the body 124. In other embodiments, including in all embodiments disclosed herein, the temperature-dependent material 112 may not be provided in a reservoir but may be provided by other means, for example the temperature dependent material 112 may be adhered to a component of the device, for example the second component, for example the temperature dependent material 112 may be adhered to the body 124.

The temperature-dependent material 112 has a temperature-dependent material characteristic such that the temperature-dependent material 112 has a first material characteristic at a first temperature of the temperature-dependent material 112 and a second material characteristic at a second temperature of the temperature-dependent material 112. The second temperature is greater (i.e. more positive) than the first temperature. Thus, in some embodiments, when the temperature of the temperature-dependent material 112 is below a predetermined temperature, the temperature-dependent material 112 exhibits a first material characteristic and, when the temperature of the temperature-dependent material 112 is above the predetermined temperature, the temperature-dependent material 112 exhibits a second material characteristic. The transition from the first material characteristic to the second material characteristic reduces the force required for the engagement member 114 to move through the temperature-dependent material 112 and thereby reduces the force required to remove the cap 118 from the body 124.

As will be appreciated, any suitable temperature-dependent material characteristic may be used. For example, in some embodiments, the viscosity of the temperature-dependent material 112 may reduce from the first temperature to the second temperature such that the force required to move the engagement member 114 with respect to the temperature-dependent material 112, and thereby to remove the cap 118, is substantially less at the second temperature than at the first temperature.

In another embodiment, a phase of the temperature-dependent material 112 may change from the first temperature to the second temperature, for example the temperature-dependent material 112 may be in a solid phase at the first temperature but the temperature-dependent material 112 may be in a liquid phase at the second temperature such that the force required to move the engagement member 114 with respect to the temperature-dependent material 112, and thereby the force required to remove the cap 118, is substantially less at the second temperature than at the first temperature.

In still other embodiments, the temperature-dependent material characteristic may be a density of the temperature-dependent material 112 such that the density for example reduces from the first temperature to the second temperature such that the force required to move the engagement member 114 with respect to the temperature-dependent material 112, and thereby the force required to remove the cap 118, is substantially less at the second temperature than at the first temperature.

In yet another embodiment, the temperature-dependent material characteristic may be a material stiffness of the temperature-dependent material 112 such that the material stiffness reduces from the first temperature to the second temperature such that the force required to move the engagement member 114 with respect to the temperature-dependent material 112, and thereby the force required to remove the cap 118, is substantially less at the second temperature than at the first temperature.

In yet another embodiment, the temperature-dependent material characteristic may be an adhesiveness (or stickiness or tackiness), of the temperature-dependent material 112 such that the adhesiveness for example reduces from the first temperature to the second temperature such that the force required to move the engagement member 114 with respect to the temperature-dependent material 112 and, thereby the force required in order to move the first and second components (in this embodiment the cap 118 and the body 124) with respect to each other, is reduced at the second temperature as compared to at the first temperature.

The temperature-dependent material 112 may be preselected according to the desired temperature-dependent material characteristic.

In the embodiment shown in FIGS. 3A and 3B, the engagement member 114 is provided as a projection 128 configured to axially extend from the cap 118 and into the temperature-dependent material 112 when the cap 118 is attached to the body 124. The projection 128 additionally comprises a radially extending lip or finger 130 at a proximal end thereof although this is not essential. The lip or finger 130 may increase the force required in order to move the engagement member 114 with respect to the temperature-dependent material 112 as the temperature-dependent material may in some embodiments form, or mold, around the lip or finger 130, for example as the temperature of the temperature-dependent material 112 changes from the second temperature to the first temperature.

In this embodiment, when the cap 118 is attached to the body 124, the engagement member 114 is in interlocking engagement with the temperature-dependent material 112 in that the engagement member 114 is received within the temperature-dependent material 112 such that when the temperature-dependent material 112 is solid (for example) at the first temperature the engagement member 114 is entrapped within the reservoir 116 by the solid temperature-dependent material 112, thereby preventing the removal of the cap 118 from the body 124. As the temperature of the temperature-dependent material 112 increases from the first temperature to the second temperature (e.g. through being passively heated by the device's external environment), the temperature-dependent material characteristic changes such that, at the second temperature, the temperature-dependent material 112 for example changes to a liquid phase such that the engagement member 114 is no longer entrapped by the temperature-dependent material 112 but the engagement member 114 is now released and so is now able to more readily move through the temperature-dependent material 112 as the user pulls on the cap 118, thereby allowing the cap 118 to be removed from the body 124 and thereby removing the engagement member 114 from the temperature-dependent material. Thus, the force the user must apply in order to remove the cap 118 is substantially less at the second temperature than at the first temperature.

In other embodiments, for example, rather than the phase of the temperature-dependent material 112 changing from the first temperature to the second temperature, a viscosity of the temperature-dependent-material 112 may reduce from the first temperature to the second temperature such that removal of the cap 118 is resisted at the first temperature but, as the viscosity at the second temperature is reduced as compared to the first temperature, the cap 118 is more readily removed as the engagement member 114 is able to more readily move through the temperature-dependent material 112. Thus, the force the user must apply in order to remove the cap 118 is substantially less at the second temperature than at the first temperature. The lip or finger 130 in such an embodiment may increase the viscous friction between the engagement member 114 and the temperature-dependent material 112.

While in this embodiment the cap 118 comprises the engagement member 114 and the body 124 comprises the temperature-dependent material 112, in other embodiments the cap 118 may instead comprise the temperature-dependent material 112 and the body 124 may instead comprise the engagement member 114. In other embodiments, the temperature-dependent material 112 may be provided elsewhere.

In other embodiments, the temperature-dependent material 112 may comprise a deflectable member configured to retain, or resist movement of, the engagement member 114 so as to fixedly couple the engagement member 114 with respect to the temperature-dependent material 112. The temperature-dependent material 112 of the deflectable member may have a first material stiffness at the first temperature and temperature-dependent material 112 may have a second, reduced material stiffness at the second temperature. In some embodiments, the first material stiffness may be such that the deflectable member is substantially rigid at the first temperature and the second material stiffness may be such that the deflectable member is substantially flexible at the second temperature so as to allow the engagement member 114 to move past the deflectable member, thereby reducing the force the user must apply in order to remove the cap 118 at the second temperature than at the first temperature.

In some embodiments, the temperature-dependent material 112 may comprise a first adhesiveness (e.g. stickiness or tackiness) at the first temperature and a second, reduced adhesiveness at the second temperature. In such embodiments, the engagement member 114 may be configured to (e.g. abuttingly or directly) engage the temperature-dependent material 112 so as to adhere thereto, requiring a first force at the first temperature in order to cause the engagement member 114 to move relative to (e.g. to separate from) the temperature-dependent material 112 and a second, reduced force at the second temperature in order to cause the engagement member 114 to move relative to (e.g. to separate from) the temperature-dependent material 112, thereby reducing the force the user must apply in order to remove the cap 118 at the second temperature than at the first temperature.

The first temperature may be any suitable temperature. For example, in certain embodiments, the first temperature is 10 degrees Celsius or less, for example 10, 9, 8, 7, 6, 5, 4, 3, 2, 1, 0, −1, −2, −3, −4, −5, −6, −7, −8, −9, −10, −11, −12, −13, −14 or −15 degrees Celsius or more, or the first temperature is within a range defined by any two of these values.

The second temperature may be any suitable temperature. For example, in certain embodiments, the second temperature may be 5 degrees Celsius or more, for example 6, 7, 8, 9, 10, 11, 12, 13, 14, 15, 16, 17, 18, 19, 20, 21, 23, 24 or 25 degrees, or the second temperature may be within a range defined by any two of these values.

In certain embodiments, the temperature-dependent material may be configured such that the temperature-dependent material characteristic changes from the first characteristic to the second characteristic across a predetermined transition temperature or temperature range.

In some embodiments, the temperature-dependent material may comprise a wax, polyethylene glycol, or a salt hydrate. Waxes in particular transition from a solid phase to a liquid phase as the temperature increases.

Turning now to FIGS. 4A to 4C, parts of a second embodiment of medicament delivery device 200 are shown. For ease of illustration, parts of the medicament delivery device 200 are shown, but it will be appreciated that the device 200 of the second embodiment may be provided with one or more of the other parts of the device 500 discussed with reference to FIGS. 2A-2G and in certain embodiments, the device 200 of the second embodiment can be considered to be a modification of the prior art device 500.

Corresponding features shared between the first and second embodiments share corresponding reference numerals, with those of the second embodiment being increased by 100 as compared to those of the first embodiment.

The medicament delivery device 200 of the second embodiment comprises a first component 206 which in this embodiment is embodied as a needle sleeve 222 and a second component 208 which in this embodiment is embodied as a body (or housing) 224. The needle sleeve 222 is axially moveable in a proximal direction from an extended position (FIGS. 4A and 4B) in which the needle sleeve 222 extends from a distal end 204 of the device to a retracted, or depressed, position (FIG. 4C). In the extended position, the needle sleeve 222 may in certain embodiments cover a needle 234 of the device so as to prevent stick injuries. The needle sleeve 222 comprises an aperture 232 provided in a distal end thereof through which the needle extends when the needle sleeve 222 is in the retracted position. When a user depresses the device 200 against an injection site, the needle sleeve 222 is caused to move axially from the extended position to the retracted position for delivering a dose of medicament through the needle 234.

The device 200 further comprises a temperature-dependent interconnect 210 configured to resist axial movement of the needle sleeve 222 from the extended position to the retracted position. The temperature-dependent interconnect 210 comprises a temperature-dependent material 212, which in this embodiment is provided in a reservoir 216, and an engagement member 214 configured to engage the temperature-dependent material.

In the same way as in the first embodiment, the temperature-dependent material 212 has a temperature-dependent material characteristic such that the temperature-dependent material 212 has a first material characteristic at a first temperature of the temperature-dependent material 212 and a second material characteristic at a second temperature of the temperature-dependent material 212. The second temperature is greater (i.e. more positive) than the first temperature. Thus, in some embodiments, when the temperature of the temperature-dependent material 212 is below a predetermined temperature, the temperature-dependent material 212 exhibits a first material characteristic and, when the temperature of the temperature-dependent material 212 is above the predetermined temperature, the temperature-dependent material 212 exhibits a second material characteristic. The transition from the first material characteristic to the second material characteristic reduces the force required for the engagement member 214 to move with respect to the temperature-dependent material 212 and thereby reduces the force required to move the needle sleeve 222 from the extended position to the retracted position.

As will be appreciated, any suitable temperature-dependent material characteristic may be used. For example, in some embodiments, the viscosity of the temperature-dependent material 212 may reduce from the first temperature to the second temperature such that the force required to move the needle sleeve 222 from the extended position to the retracted position is substantially less at the second temperature than at the first temperature.

In other embodiments, a phase of the temperature-dependent material 212 may change from the first temperature to the second temperature, for example the temperature-dependent material 212 may be in a solid phase at the first temperature but the temperature-dependent material 212 may be in a liquid phase at the second temperature such that the force required in order to move the engagement member 214 with respect to the temperature-dependent material 212, and thereby the force required to move the first 206 and second 208 components (in this embodiment the needle sleeve 222 and the body 224 respectively) with respect to each other, is reduced at the second temperature as compared to at the first temperature.

In still other embodiments, the temperature-dependent material characteristic may be a density of the temperature-dependent material 212 such that the density of the temperature-dependent material 212 reduces from the first temperature to the second temperature such that the force required in order to move the engagement member 214 with respect to the temperature-dependent material 212, and thereby the force required to move the first 206 and second 208 components (in this embodiment the needle sleeve 222 and the body 224 respectively) with respect to each other, is reduced at the second temperature as compared to at the first temperature.

In yet another embodiment, the temperature-dependent material characteristic may be a material stiffness of the temperature-dependent material 212 such that the material stiffness for example reduces from the first temperature to the second temperature such that the force required in order to move the engagement member 214 with respect to the temperature-dependent material 212, and thereby the force required to move the first and second components (in this embodiment the needle sleeve 222 and the body 224 respectively) with respect to each other, is reduced at the second temperature as compared to at the first temperature.

In yet another embodiment, the temperature-dependent material characteristic may be an adhesiveness, or stickiness or tackiness, of the temperature-dependent material 212 such that the adhesiveness for example reduces from the first temperature to the second temperature such that the force required in order to move the engagement member 214 with respect to the temperature-dependent material 212, and thereby the force required in order to move the first and second components (in this embodiment the needle sleeve 222 and the body 224 respectively) with respect to each other, is reduced at the second temperature as compared to at the first temperature.

The temperature-dependent material 212 may be preselected according to the desired temperature-dependent material characteristic.

In the embodiment shown in FIGS. 4A to 4C, a proximal end of the needle sleeve 222 comprises the engagement member 214. The engagement member 214 is configured to extend into the reservoir 216 so as to be received within the temperature-dependent material 212 when the needle sleeve 222 is both in the extended and retracted positions. As the needle sleeve 222 moves from the extended position to the retracted position, the engagement member 214 is caused to move through the temperature-dependent material 212 in the reservoir 216. At the first temperature, the axial movement of the needle sleeve 222 is resisted by the temperature-dependent material 212 to a greater extent that at the second temperature due to the change in material characteristic of the temperature-dependent material 212 from the first temperature to the second temperature. In some embodiments, the axial movement of the needle sleeve 222 may be substantially prevented at the first temperature. In some embodiments, the temperature-dependent material 212 may change from a solid phase at the first temperature to a liquid phase at the second temperature, thereby more readily allowing the needle sleeve 222 to move to the retracted position. Thus, at the second temperature, a reduced force is required in order to move the needle sleeve 222 from the extended position to the retracted position.

FIG. 4A shows the temperature-dependent material 212 at the first temperature, FIG. 4B shows the temperature-dependent material 212 after it has warmed to the second temperature and FIG. 4C shows the axial movement of the needle sleeve 222 to the retraced position once the temperature-dependent material 212 has reached the second temperature.

In other embodiments, for example rather than the phase of the temperature-dependent material 212 changing from the first temperature to the second temperature, instead a viscosity of the temperature-dependent material may reduce from the first temperature to the second temperature such that movement of the needle sleeve 222 to the retracted position is resisted at the first temperature but, as the viscosity at the second temperature is reduced as compared to the first temperature, the needle sleeve 222 is more readily moved to the retracted position as the engagement member 214 is able to more readily move through the temperature-dependent material 212. Thus, the force required in order to move the needle sleeve 222 to the retracted position is less at the second temperature than at the first temperature.

While in this embodiment the needle sleeve 222 comprises the engagement member 214 and the body 224 comprises the temperature-dependent material 212, in other embodiments the needle sleeve 222 may instead comprise the temperature-dependent material 212 and the body 224 may instead comprise the engagement member 214. In other embodiments, the temperature-dependent material 212 may be provided elsewhere.

In other embodiments, the temperature-dependent material 212 may comprise a deflectable member configured to retain, or resist movement of, the engagement member 214 so as to fixedly couple the engagement member 214 with respect to the temperature-dependent material 212. The temperature-dependent material 212 of the deflectable member may have a first material stiffness at the first temperature but the temperature-dependent material 212 may have a second, reduced material stiffness at the second temperature. In some embodiments, the first material stiffness may be such that the deflectable member is substantially rigid at the first temperature and the second material stiffness may be such that the deflectable member is substantially flexible at the second temperature so as to allow the engagement member 214 to move past the deflectable member, thereby reducing the force required to move the needle sleeve 222 from the extended position to the retracted position.

In other embodiments, the temperature-dependent material 212 may comprise a first adhesiveness (e.g. stickiness or tackiness) at the first temperature and a second, reduced adhesiveness at the second temperature. In such embodiments, the engagement member 214 may be configured to engage the temperature-dependent material 212 so as to adhere thereto, requiring a first force at the first temperature in order to cause the engagement member 214 to move relative to (e.g. through) the temperature-dependent material 212 and a second, reduced force at the second temperature in order to cause the engagement member 214 to move relative to the temperature-dependent material 212.

Turning now to FIGS. 5A to 5C, parts of a third embodiment of medicament delivery device 300 are shown. For ease of illustration, parts of the medicament delivery device 300 are shown, but it will be appreciated that the device 300 of the third embodiment may be provided with one or more of the other parts of the device 500 discussed with reference to FIGS. 2A-2G and in certain embodiments, the device 300 of the third embodiment can be considered to be a modification of the device 500.

Corresponding features shared between the first and third embodiments share corresponding reference numerals, with those of the third embodiment being increased by 200 as compared to those of the first embodiment.

The medicament delivery device 300 of the third embodiment comprises a first component 306 which in this embodiment is embodied as an actuation member 320 comprising a button 320 (although other actuation members could instead be used) and a second component 308 which in this embodiment is embodied as a body (or housing) 324. The button 320 is configured to be moved (e.g. depressed) by a user from a first position (FIGS. 5A and 5B) to an actuation position (FIG. 5C) for dispensing medicament from the device. In the actuation position, the actuation member 320 may trigger the dispensing of medicament from the device, for example the actuation member 320 may cause a syringe of the device to move distally so as to cause a needle of the syringe to move distally from a covered position in which the needle is covered by the body 324 to an uncovered position in which the needle is exposed from a distal end of the body 324 for delivering medicament. Alternatively or additionally, movement of the actuation member 320 to the actuation position may trigger the release of a plunger to move the plunger with respect to the syringe so as to dispense medicament within the syringe through the needle.

The device 300 further comprises a temperature-dependent interconnect 310 configured to resist axial movement of the actuation member 320 from the first position to the actuation position. The temperature-dependent interconnect 310 comprises a temperature-dependent material 312, which in this embodiment is provided in a reservoir 316, and an engagement member 314 configured to engage the temperature-dependent material 312.

In the same way as in the first embodiment, the temperature-dependent material 312 has a temperature-dependent material characteristic such that the temperature-dependent material 312 has a first material characteristic at a first temperature of the temperature-dependent material 312 and a second material characteristic at a second temperature of the temperature-dependent material 312. The second temperature is greater than the first temperature. Thus, in some embodiments, when the temperature of the temperature-dependent material 312 is below a predetermined temperature, the temperature-dependent material 312 exhibits a first material characteristic and, when the temperature of the temperature-dependent material 312 is above the predetermined temperature, the temperature-dependent material 312 exhibits a second material characteristic. The transition from the first material characteristic to the second material characteristic reduces the force required for the engagement member 314 to move with respect to the temperature-dependent material 312 and thereby reduces the force required to move the actuation member 320 from the first position to the actuation position.

As will be appreciated, any suitable temperature-dependent material characteristic may be used. For example, in some embodiments, the viscosity of the temperature-dependent material 312 may reduce from the first temperature to the second temperature such that the force required to move the actuation member 320 from the first position to the actuation position is substantially less at the second temperature than at the first temperature.

In other embodiments, a phase of the temperature-dependent material 312 may change from the first temperature to the second temperature, for example the temperature-dependent material 312 may be in a solid phase at the first temperature but the temperature-dependent material 312 may be in a liquid phase at the second temperature such that the force required in order to move the first and second components (in this embodiment the actuation member 320 and the body 324 respectively) with respect to each other is reduced at the second temperature as compared to at the first temperature.

In still other embodiments, the temperature-dependent material characteristic may be a density of the temperature-dependent material 312 such that the density of the temperature-dependent material reduces from the first temperature to the second temperature such that the force required in order to move the first and second components (in this embodiment the actuation member 320 and the body 324 respectively) with respect to each other is reduced at the second temperature as compared to at the first temperature.

In yet another embodiment, the temperature-dependent material characteristic may be a material stiffness of the temperature-dependent material 312 such that the material stiffness for example reduces from the first temperature to the second temperature such that the force required in order to move the first and second components (in this embodiment the actuation member 320 and the body 324 respectively) with respect to each other is reduced at the second temperature as compared to at the first temperature.

In yet another embodiment, the temperature-dependent material characteristic may be an adhesiveness, or stickiness or tackiness, of the temperature-dependent material 312 such that the adhesiveness for example reduces from the first temperature to the second temperature such that the force required in order to move the first and second components (in this embodiment the actuation member 320 and the body 324 respectively) with respect to each other is reduced at the second temperature as compared to at the first temperature.

The temperature-dependent material 312 may be preselected according to the desired temperature-dependent material characteristic.

In the embodiment shown in FIGS. 5A to 5C, the engagement member 214 is substantially U-shaped, having a first leg 336 which extends from an underside distal surface of the button 320 and a second leg 338 which is configured to extend into the reservoir 316 so as to be received within the temperature-dependent material 312 when the button 320 is in the first position. As the button 320 is moved from the first position to the actuation position, the second leg 338 is caused to move through the temperature-dependent material 312 in the reservoir 316.

At the first temperature, the movement of the button 320 from the first position to the actuation position is resisted by the temperature-dependent material 312 to a greater extent that at the second temperature due to the change in material characteristic of the temperature-dependent material 312 from the first temperature to the second temperature. In some embodiments, the temperature-dependent material 312 may change from a solid phase at the first temperature to a liquid phase in the second temperature, thereby more readily allowing the button 320 to move to the actuation position. Thus, at the second temperature, a reduced force is required in order to move the button 320 from the extended position to the retracted position.

FIG. 5A shows the temperature-dependent material 312 at the first temperature, FIG. 5B shows the temperature-dependent material 312 after the temperature-dependent material 312 has warmed to the second temperature and FIG. 5C shows the movement of the actuation member 320, being depressed by a user, to the actuation position once the temperature-dependent material 312 has reached the second temperature.

In other embodiments, for example rather than the phase of the temperature-dependent material 312 changing from the first temperature to the second temperature, instead a viscosity of the temperature-dependent material may reduce from the first temperature to the second temperature such that movement of the actuation member 320 to the actuation position is resisted at the first temperature but, as the viscosity at the second temperature is reduced as compared to the first temperature, the actuation member 320 is more readily moved to the actuation position as the engagement member 314 is able to more readily move through the temperature-dependent material 312. Thus, the force required in order to move the actuation member 320 to the actuation position is less at the second temperature than at the first temperature.

While in this embodiment the actuation member 320 comprises the engagement member 314 and the body 324 comprises the temperature-dependent material 312, in other embodiments the actuation member 314 may instead comprise the temperature-dependent material 312 and the body 324 may instead comprise the engagement member 314. In other embodiments, the temperature-dependent material 312 may be provided elsewhere.

In other embodiments, the temperature-dependent material 312 may comprise a deflectable member configured to retain, or resist movement of, the engagement member 314 so as to fixedly couple the engagement member 314 with respect to the temperature-dependent material 312. The temperature-dependent material 312 of the deflectable member may have a first material stiffness at the first temperature and it may have a second, reduced material stiffness at the second temperature. In some embodiments, the first material stiffness may be such that the deflectable member is substantially rigid at the first temperature and the second material stiffness may be such that the deflectable member is substantially flexible at the second temperature so as to allow the engagement member 314 to move past the deflectable member, thereby reducing the force required to move the actuation member 320 from the first position to the actuation position.

In other embodiments, the temperature-dependent material 312 may comprise a first adhesiveness (e.g. stickiness or tackiness) at the first temperature and a second, reduced adhesiveness at the second temperature. In such embodiments, the engagement member 314 may be configured to engage the temperature-dependent material 312 so as to adhere thereto, requiring a first force at the first temperature in order to cause the engagement member 314 to move relative to (e.g. through) the temperature-dependent material 312 and a second, reduced force at the second temperature in order to cause the engagement member 314 to move relative to the temperature-dependent material 312.

Turning now to FIGS. 6A to 6C, parts of a fourth embodiment of medicament delivery device 400 are shown. For ease of illustration, parts of the medicament delivery device 400 are shown, but it will be appreciated that the device 400 of the fourth embodiment may be provided with one or more of the other parts of the device 500 discussed with reference to FIGS. 2A-2G and in certain embodiments, the device 400 of the fourth embodiment can be considered to be a modification of the device 500.

Corresponding features shared between the first and fourth embodiments share corresponding reference numerals, with those of the fourth embodiment being increased by 300 as compared to those of the first embodiment.

The medicament delivery device 400 of the fourth embodiment comprises a first component 406 which in this embodiment is embodied as a locking member 440, and a second component 408 which in this embodiment is embodied as a reservoir 416. In other embodiments the second component 408 may be body or housing of the device, although the second component 408 may in other embodiments be any other component of the device that the locking member 440 is rotatable with respect to, for example a component which is rotationally coupled with the body or housing. In this embodiment, the reservoir 416 is rotationally coupled to the housing.

The device 400 comprises an actuation member 420 configured to be moveable by a user from a first position to an actuation position to cause medicament to be dispensed from the medicament delivery device. In this embodiment, the actuation member 420 comprises a button 420 provided at a proximal end of the device 400, the button 420 being depressible by a user in a distal direction from the first position to the actuation position. In the actuation position, the actuation member 420 may trigger the dispensing of medicament from the device, for example the actuation member 420 may cause a syringe of the device to move distally so as to cause a needle of the syringe to move distally from a covered position in which the needle is covered by the body to an uncovered position in which the needle is exposed from a distal end of the body for delivering medicament. Alternatively or additionally, movement of the actuation member 420 to the actuation position may trigger the release of a plunger to move the plunger with respect to the syringe so as to dispense medicament within the syringe through the needle.

The locking member 440 is rotationally coupled to the button 420 such that rotation of the locking member causes rotation of the button 420. The locking member 440 is rotatable with respect to the second component 408, e.g. about a longitudinal axis of the device, from a locking position (FIGS. 6A and 6B), in which the button 420 is prevented from being depressed by a user, to an actuation member release position (FIG. 6C) in which the button 420 is released so as to allow the button 420 to be depressed by a user to the actuation position.

The button 420 comprises a blocking member 462 which in this embodiment is embodied as an axially extending protrusion 462, although any other suitable blocking member may instead be used. In the locking position shown in FIGS. 6A and 6B, the blocking member 462 is in abutting engagement with an actuation member support 446, thereby preventing the button 420 from being depressed to the actuation position.

As shown in FIG. 6C, rotation of the locking member 440, for example by a user, from the locking position to the actuator member release position causes the button 420 to rotate with the locking member 440 such that, in the actuation member release position, the blocking member 462 aligns with an aperture 448 provided in the actuation member support 446 such that the blocking member 462 is able to be received within the aperture 448 when the button 420 is moved to the actuation position, thereby removing the blocking engagement between the blocking member 462 and the actuation member support 446. Thus, in the actuation member release position, the button 420 is now able to be depressed by a user to the actuation position. In other embodiments, the aperture 448 may be provided in the button 420 and the blocking member 462 may be provided in another component of the device 400 other than the actuation member support 446 provided that the button 420 is rotational with respect to the component such that movement of the locking member 440 to the actuation member release position causes the aperture 448 and the blocking member 462 to align such that the aperture 448 may receive the blocking member 462 in the actuation position in order to remove the previous blocking engagement therebetween.

The device 400 further comprises a temperature-dependent interconnect 410 configured to resist movement of the locking member 440 from the locking position to the actuation member release position. The temperature-dependent interconnect 410 comprises a temperature-dependent material 412, which in this embodiment is provided in the reservoir 416, and an engagement member 414 configured to engage the temperature-dependent material 412.

In the same way as in the first embodiment, the temperature-dependent material 412 has a temperature-dependent material characteristic such that the temperature-dependent material 412 has a first material characteristic at a first temperature of the temperature-dependent material 412 and a second material characteristic at a second temperature of the temperature-dependent material 412. The second temperature is greater than the first temperature. Thus, in some embodiments, when the temperature of the temperature-dependent material 412 is below a predetermined temperature, the temperature-dependent material 412 exhibits a first material characteristic and, when the temperature of the temperature-dependent material 412 is above the predetermined temperature, the temperature-dependent material 412 exhibits a second material characteristic. The transition from the first material characteristic to the second material characteristic reduces the force required for the engagement member 414 to move with respect to the temperature-dependent material 412 and thereby reduces the force required to move the locking member 440 from the locking position to the actuator release position. In the embodiment of FIGS. 6A to 6C, the engagement member 414 comprises a radially extending paddle 442 rotationally coupled to the locking member 440, the paddle 442 being configured to rotate within the temperature-dependent material 412 at the second temperature as the locking member 440 is moved from the locking position to the actuation member release position but whose rotation is resisted by the temperature-dependent material 412 at the first temperature. In this embodiment the paddle 442 is rotationally coupled to the locking member 440 by an axially extending shaft 452, although any other suitable configuration may instead be used.

As will be appreciated, any suitable temperature-dependent material characteristic may be used. For example, in some embodiments, the viscosity of the temperature-dependent material 412 may reduce from the first temperature to the second temperature such that the force required to move the locking member 440 from the locking position to the actuation member release position is substantially less at the second temperature than at the first temperature.

In other embodiments, a phase of the temperature-dependent material 412 may change from the first temperature to the second temperature, for example the temperature-dependent material 412 may be in a solid phase at the first temperature but the temperature-dependent material 412 may be in a liquid phase at the second temperature such that the force required in order to move the locking member 440 from the locking position to the actuation member release position at the second temperature is reduced as compared to at the first temperature.

In still other embodiments, the temperature-dependent material characteristic may be a density of the temperature-dependent material 412 such that the density of the temperature-dependent material 412 reduces from the first temperature to the second temperature such that the force required in order to move the locking member 440 from the locking position to the actuation member release position is reduced at the second temperature as compared to at the first temperature.

In yet another embodiment, the temperature-dependent material characteristic may be a material stiffness of the temperature-dependent material 412 such that the material stiffness for example reduces from the first temperature to the second temperature such that the force required in order to move the locking member 440 from the locking position to the actuation member release position is reduced at the second temperature as compared to at the first temperature.

In yet another embodiment, the temperature-dependent material characteristic may be an adhesiveness, or stickiness or tackiness, of the temperature-dependent material 412 such that the adhesiveness for example reduces from the first temperature to the second temperature such that the force required in order to move the locking member 440 from the locking position to the actuation member release position is reduced at the second temperature as compared to at the first temperature.

The temperature-dependent material 412 may be preselected according to the desired temperature-dependent material characteristic.

In other embodiments, for example rather than the phase of the temperature-dependent material 412 changing from the first temperature to the second temperature, instead a viscosity of the temperature-dependent material may reduce from the first temperature to the second temperature such that movement of the locking member 440 to the actuation member release position 440 is resisted at the first temperature but, as the viscosity at the second temperature is reduced as compared to the first temperature, the locking member 440 is more readily moved to the actuation member release position as the engagement member 414 is able to more readily move through the temperature-dependent material 412. Thus, the force required in order to move the locking member 440 to the actuation member release position is less at the second temperature than at the first temperature.

In other embodiments, the temperature-dependent material 412 may comprise a deflectable member configured to retain, or resist movement of, the engagement member 414 so as to fixedly couple the engagement member 414 with respect to the temperature-dependent material 412. The temperature-dependent material 412 of the deflectable member may have a first material stiffness at the first temperature and it may have a second, reduced material stiffness at the second temperature. In some embodiments, the first material stiffness may be such that the deflectable member is substantially rigid at the first temperature and the second material stiffness may be such that the deflectable member is substantially flexible at the second temperature so as to allow the engagement member 414 to move past the deflectable member, thereby reducing the force required to move the locking member 440 from the locking position to the actuation member release position.

In other embodiments, the temperature-dependent material 412 may comprise a first adhesiveness (e.g. stickiness or tackiness) at the first temperature and a second, reduced adhesiveness at the second temperature. In such embodiments, the engagement member 414 may be configured to engage the temperature-dependent material 412 so as to adhere thereto, requiring a first force at the first temperature in order to cause the engagement member 414 to move relative to (e.g. through) the temperature-dependent material 412 and a second, reduced force at the second temperature in order to cause the engagement member 414 to move relative to the temperature-dependent material 412.

The operation of the device of the fourth embodiment will now be described with reference to FIGS. 6A to 6C.

In a pre-use configuration shown in FIG. 6A, as the blocking member 462 is misaligned with the aperture 448, the blocking member 462 is in blocking engagement with the actuation member support 446 such that the button 420 is unable to be depressed by a user from the first position to the actuation position for dispensing medicament from the device 400. The temperature-dependent material 412 within the reservoir 416 is at the first temperature and so resists rotation of the paddle 442 within the temperature-dependent material 412. As the paddle 442 is rotationally coupled to the locking member 440 by way of shaft 452, movement of the locking member 440 to the actuation member release position is resisted by the temperature-dependent material 412. In some embodiments, at the first temperature, movement of the paddle 442 within the temperature-dependent material 412 is substantially prevented such that movement of the locking member 440 to the actuation member release position is substantially prevented.

In FIG. 6B, the temperature of temperature-dependent material 412 has increased to the second temperature such that a reduced force is required in order to rotate paddle 442 within the temperature-dependent material 412 as compared to at the first temperature. Thus, the force required to move the locking member 440 from the locking position to the actuation member release position is reduced at the second temperature compared to at the first temperature. The user is thus more readily able to rotate the locking member 440 from the locking position to the actuation member release position.

In FIG. 6C, with the temperature of the temperature-dependent material 412 now at the second temperature, the user rotates the locking member 440 from the locking position to the actuation member release position, thereby causing the paddle 442 to rotate within the temperature-dependent material 412 in the reservoir 416. As the button 420 is rotationally coupled to the locking member 440, rotation of the locking member 440 to the actuation member release position causes the button 420 to rotate therewith, thereby causing the blocking member 462 to align with the aperture 448 provided in the actuation member support 446, thereby removing the blocking engagement between the blocking member 462 and the actuation member support 446. The button 420 is now able to be depressed by a user from the first position to the actuation position. The user then depresses the button 420 to the actuation position, causing the blocking member 462 to be received within the aperture 448 and, in some embodiments, causing the device to dispense medicament from the needle. As explained above, the actuation member 420 (button 420) being moved to the actuation position may cause the needle to move from a covered position to an uncovered position for being received at an injection site for dispending of medicament or alternatively or additionally the movement of the actuation member 420 to the actuation position may cause a plunger of the device to be released so as to cause the plunger to move within a syringe of the device so as to cause medicament to be dispensed through the needle.

In all embodiments disclosed herein, where the temperature-dependent materials 112; 212; 312; and/or 412 are not contained within the reservoir and so may escape the reservoirs 116; 216; 316; and/or 416 at the second temperature (for example wherein the temperature-dependent materials 112; 212; 312; and/or 414 are in a liquid or gaseous phase at the second temperature), the engagement members 114; 214; 314; and/or 414 may be considered to instead move with respect to the reservoirs 116; 216; 316; and/or 416 at the second temperature rather than with respect to the temperature-dependent material 112; 212; 312; 412 as described above.

LIST OF FEATURES

- 10—Device
- 11—housing
- 12—cap
- 13—needle sleeve
- 17—needle
- 20—distal region
- 21—proximal region
- 22—button
- 23—piston
- 100—Device
- 104—Distal end
- 106—First component
- 108—Second component
- 110—Temperature-dependent interconnect
- 112—Temperature-dependent material
- 114—Engagement member
- 116—Reservoir
- 118—Cap
- 124—Body
- 128—Projection
- 130—Lip
- 200—Device
- 204—Distal end
- 206—First component
- 208—Second component
- 210—Temperature-dependent interconnect
- 212—Temperature-dependent material
- 214—Engagement member
- 216—Reservoir
- 222—Needle sleeve
- 224—Body
- 232—Aperture
- 234—Needle
- 300—Device
- 304—Distal end
- 306—First component
- 308—Second component
- 310—Temperature-dependent interconnect
- 312—Temperature-dependent material
- 314—Engagement member
- 316—Reservoir
- 320—Actuation member
- 324—Body
- 336—First leg of engagement member
- 338—Second leg of engagement member
- 400—Device
- 404—Distal end
- 406—First component
- 408—Second component
- 410—Temperature-dependent interconnect
- 412—Temperature-dependent material
- 414—Engagement member
- 416—Reservoir
- 420—Actuation member
- 440—Locking member
- 442—Paddle
- 446—Actuation member support
- 448—Aperture
- 450—Blocking member
- 452—Shaft
- 462—Blocking member
- 500—Device
- 504—Distal end
- 518—Cap
- 520—Actuation member
- 524—Body
- 526—Locking member
- 591—Syringe
- 592—Needle
- 593—Plunger
- 594—Injection site
- 595—Lock ring
- 596—Stop
- 597—Bias
- 598—Bias The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the devices and methods described herein include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A medicament delivery device comprising:
   a housing having a distal portion and a proximal portion, the housing defining an opening for a medicament container containing a medicament such that when the medicament container is in the housing a needle attached to the medicament container is disposed within the distal portion of the housing;
   a reservoir disposed in or on the housing, the reservoir having a distal opening for accessing an interior of the reservoir, the distal opening located radially outward of an inner wall of the reservoir, the interior of the reservoir containing a temperature-dependent material having a first material characteristic at a first temperature and a second material characteristic at a second temperature; and a cap configured to be removably attached to the distal portion of the housing to limit access to the needle when the medicament container is in the housing, the cap comprising a proximally-extending portion that extends proximally into the temperature-dependent material in the reservoir when the cap is attached to the distal portion of the housing to (i) limit a removal of the cap from the distal portion of the housing when the temperature-dependent material is at the first temperature and (ii) allow the removal of the cap from the distal portion of the housing when the temperature-dependent material is at the second temperature, wherein the medicament delivery device is configured such that a proximal end of the proximally-extending portion of the cap moves distally from the interior of the reservoir and through the distal opening of the reservoir during the removal of the cap from the distal portion of the housing, and wherein the proximal end of the proximally-extending portion of the cap comprises an outward projection disposed in the temperature-dependent material when the cap is attached to the distal portion of the housing.

2. The medicament delivery device of claim 1, wherein the second temperature is greater than the first temperature, and the temperature-dependent material comprises a wax, polyethylene glycol, or a salt hydrate.

3. The medicament delivery device of claim 1, comprising a locking member located at the proximal portion of the housing, the locking member configured to rotate relative to the housing between (i) a locked position in which axial movement of an actuation member is limited and (ii) a released position in which axial movement of the actuation member allowed.

4. The medicament delivery device of claim 3, comprising the actuation member, the actuation member configured to be axially movable relative to the housing when the locking member is in the released position to allow the medicament delivery device to dispense the medicament from the medicament container through the needle.

5. The medicament delivery device of claim 1, wherein the reservoir is disposed at the distal portion of the housing.

6. The medicament delivery device of claim 1, wherein when the temperature-dependent material is at the first temperature, the temperature-dependent material is in a solid phase and when the temperature-dependent material is at the second temperature, the temperature-dependent material is in a liquid phase.

7. The medicament delivery device of claim 1, wherein when the temperature-dependent material is at the first temperature, the temperature-dependent material is in a liquid phase and when the temperature-dependent material is at the second temperature, the temperature-dependent material is in a gaseous phase.

8. The medicament delivery device of claim 1, comprising the medicament container disposed in the housing.

9. The medicament delivery device of claim 1, wherein the outward projection is configured to provide an axial resistance force between the temperature-dependent material and the cap to limit axial movement of the cap when the temperature-dependent material is at the first temperature during an attempted removal of the cap from the distal portion of the housing.

10. A medicament delivery device comprising:
a housing having a distal portion and a proximal portion, the housing defining an opening for a medicament container, the medicament container being configured to allow a medicament to be dispensed through a needle;

a reservoir disposed in or on the housing, the reservoir comprising a proximal wall and a distally-extending wall extending distally from a radially inward portion of the proximal wall, the reservoir having a distal opening located radially outward of a distal portion of the distally-extending wall, the reservoir containing a temperature-dependent material having a first material characteristic at a first temperature and a second material characteristic at a second temperature; and a cap configured to be removably attached to the distal portion of the housing to cover the needle or a needle shield covering the needle when the medicament container is in the housing, the cap comprising a proximally-extending portion that extends proximally into the temperature-dependent material in the reservoir when the cap is attached to the distal portion of the housing to (i) limit a removal of the cap from the distal portion of the housing when the temperature-dependent material is at the first temperature and (ii) allow the removal of the cap from the distal portion of the housing when the temperature-dependent material is at the second temperature, wherein the medicament delivery device is configured such that the proximally-extending portion of the cap moves distally through the distal opening of the reservoir during the removal of the cap from the distal portion of the housing, and wherein a proximal end of the proximally-extending portion of the cap comprises an outward projection disposed in the temperature-dependent material when the cap is attached to the distal portion of the housing.

11. The medicament delivery device of claim 10, wherein the second temperature is greater than the first temperature, and the temperature-dependent material comprises a wax, polyethylene glycol, or a salt hydrate.

12. The medicament delivery device of claim 10, wherein the outward projection is configured to provide an axial resistance force between the temperature-dependent material and the cap to limit axial movement of the cap when the temperature-dependent material is at the first temperature during an attempted removal of the cap from the distal portion of the housing.

13. The medicament delivery device of claim 10, wherein the medicament delivery device is configured to dispense the medicament from the medicament container through the needle after the cap has been removed from the distal portion of the housing.

14. The medicament delivery device of claim 10, wherein the cap comprises a body portion that extends diametrically across the housing when the cap is attached to the distal portion of the housing, and the proximally-extending portion extends from a proximal side of the body portion of the cap.

15. The medicament delivery device of claim 14, wherein the proximally-extending portion is a first proximally-extending portion and the cap comprises a second proximally-extending portion extending from the proximal side of the body portion of the cap.

16. The medicament delivery device of claim 15, wherein the first proximally-extending portion and the second proximally-extending portion are disposed at diametrically opposite positions on the body portion of the cap.

17. A medicament delivery device comprising:
a housing sized for a medicament container;
a reservoir comprising an axial wall and having a distal opening located radially outward of the axial wall, the reservoir containing a temperature-dependent material having a first material characteristic at a first temperature and a second material characteristic at a second temperature; and
a cap configured to be removably attached to the housing, the cap comprising a portion that extends axially within the housing and into the temperature-dependent material in the reservoir when the cap is attached to the housing to (i) limit a removal of the cap from the housing when the temperature-dependent material is at the first temperature and (ii) allow the removal of the cap from the housing when the temperature-dependent material is at the second temperature,
wherein the medicament delivery device is configured such that a proximal end of the portion of the cap moves distally through the distal opening of the reservoir during the removal of the cap from the housing, and the medicament delivery device is configured to dispense a medicament from the medicament container when the medicament container is in the housing after removal of the cap from the housing, and
wherein the proximal end of the portion of the cap comprises an outward projection disposed in the temperature-dependent material when the cap is attached to the housing.

18. The medicament delivery device of claim 17, wherein when the temperature-dependent material is at the first temperature, the temperature-dependent material is in a solid phase and when the temperature-dependent material is at the second temperature, the temperature-dependent material is in a liquid phase.

19. The medicament delivery device of claim 18, wherein the second temperature is greater than the first temperature, and the temperature-dependent material comprises a wax, polyethylene glycol, or a salt hydrate.

20. The medicament delivery device of claim 17, wherein the cap is configured to cover an injection needle of the medicament delivery device when the cap is attached to the housing, and the medicament delivery device is configured to move the injection needle relative to the housing for allowing the injection needle to penetrate an injection site.

21. The medicament delivery device of claim 17, comprising the medicament container disposed in the housing, the medicament container containing the medicament.

22. The medicament delivery device of claim 21, wherein the medicament delivery device is configured to dispense the medicament from the medicament container after the cap has been removed from the housing.

23. The medicament delivery device of claim 17, wherein the outward projection is configured to provide an axial resistance force between the temperature-dependent material and the cap to limit axial movement of the cap when the temperature-dependent material is at the first temperature during an attempted removal of the cap from the housing.

24. A medicament delivery device comprising:
a housing comprising a reservoir comprising an axially-extending wall and having a first opening located radially outward of the axially-extending wall, the reservoir containing a temperature-dependent material having a first material characteristic at a first temperature and a second material characteristic at a second temperature; and
a cap configured to be removably attached to the housing to cover a second opening of the housing, a portion of the cap extending into the temperature-dependent material in the reservoir when the cap is attached to the housing to (i) limit a removal of the cap from the housing when the temperature-dependent material is at the first temperature and (ii) allow the removal of the cap from the housing when the temperature-dependent material is at the second temperature,
wherein the medicament delivery device is configured such that a proximal end of the portion of the cap moves distally through the first opening of the reservoir and through the second opening of the housing during the removal of the cap from the housing, and the medicament delivery device is configured to, after the cap has been removed from the housing, move a needle through the second opening of the housing and dispense a medicament through the needle, and
wherein the portion of the cap extending axially into the temperature-dependent material in the reservoir is radially outward of a longitudinal axis of the housing when the cap is attached to the housing.

25. The medicament delivery device of claim 24, wherein the second temperature is 5 degrees Celsius or greater, and the temperature-dependent material comprises a wax, polyethylene glycol, or a salt hydrate.

26. The medicament delivery device of claim 24, comprising a medicament container disposed in the housing, the medicament container comprising the needle configured to be inserted into an injection site, the medicament container containing the medicament configured to be delivered into the injection site.

27. The medicament delivery device of claim 24, wherein the portion of the cap extending axially into the temperature-dependent material in the reservoir that is radially outward of the longitudinal axis of the housing when the cap is attached to the housing is configured to provide an axial resistance force between the temperature-dependent material and the cap to limit axial movement of the cap when the temperature-dependent material is at the first temperature during an attempted removal of the cap from the housing.

* * * * *

UNITED STATES PATENT AND TRADEMARK OFFICE
CERTIFICATE OF CORRECTION

PATENT NO. : 12,357,758 B1  
APPLICATION NO. : 18/640292  
DATED : July 15, 2025  
INVENTOR(S) : Alexander Hee-Hanson et al.

Page 1 of 1

It is certified that error appears in the above-identified patent and that said Letters Patent is hereby corrected as shown below:

In the Claims

Column 33, Line 41, Claim 3, after "member", insert -- is --

Signed and Sealed this  
Second Day of September, 2025

Coke Morgan Stewart  
*Acting Director of the United States Patent and Trademark Office*